(12) United States Patent
Nelson et al.

(10) Patent No.: US 8,892,207 B2
(45) Date of Patent: Nov. 18, 2014

(54) ELECTRICAL THERAPY FOR FACILITATING INTER-AREA BRAIN SYNCHRONIZATION

(75) Inventors: Dwight E. Nelson, Shoreview, MN (US); Rahul Gupta, Roseville, MN (US)

(73) Assignee: Medtronic, Inc., Minneapolis, MN (US)

(*) Notice: Subject to any disclaimer, the term of this patent is extended or adjusted under 35 U.S.C. 154(b) by 228 days.

(21) Appl. No.: 13/446,678

(22) Filed: Apr. 13, 2012

(65) Prior Publication Data

US 2012/0271374 A1    Oct. 25, 2012

Related U.S. Application Data

(60) Provisional application No. 61/477,346, filed on Apr. 20, 2011.

(51) Int. Cl.
| | | |
|---|---|---|
| *A61N 1/00* | (2006.01) | |
| *A61N 1/36* | (2006.01) | |
| *A61N 1/05* | (2006.01) | |
| A61B 5/0484 | (2006.01) | |
| A61B 5/0476 | (2006.01) | |

(52) U.S. Cl.
CPC .......... *A61N 1/0534* (2013.01); *A61N 1/36082* (2013.01); *A61N 1/36139* (2013.01); *A61B 5/0484* (2013.01); *A61N 1/36185* (2013.01); *A61B 5/0476* (2013.01)
USPC .......................................................... 607/45

(58) Field of Classification Search
CPC ............ A61N 1/36082; A61N 1/0534; A61N 1/36067; A61N 1/36025
USPC .................................................. 607/45, 3, 2
See application file for complete search history.

(56) References Cited

U.S. PATENT DOCUMENTS

| | | |
|---|---|---|
| 4,227,516 A | 10/1980 | Meland et al. |
| 4,753,246 A | 6/1988 | Freeman |
| 4,776,345 A | 10/1988 | Cohen et al. |
| 5,299,569 A | 4/1994 | Wernicke et al. |
| 6,157,857 A | 12/2000 | Dimpfel |
| 6,167,298 A | 12/2000 | Levin |
| 6,200,273 B1 | 3/2001 | Sininger |
| 6,227,203 B1 | 5/2001 | Rise et al. |
| 6,402,520 B1 | 6/2002 | Freer |
| 6,453,193 B1 | 9/2002 | Heyrend et al. |
| 6,615,076 B2 | 9/2003 | Mitra |
| 6,920,351 B2 | 7/2005 | Mitra |

(Continued)

OTHER PUBLICATIONS

Eusebio, et al., "Resonance in Subthatamo-Cortical Circuits in Parkinson's Disease", Brain 2009, pp. 1-12.

(Continued)

*Primary Examiner* — Christopher D Koharski
*Assistant Examiner* — Philip Edwards
(74) *Attorney, Agent, or Firm* — Shumaker & Sieffert, P.A.

(57) ABSTRACT

Methods and apparatuses are described for monitoring synchronization of two or more brain areas and delivering an electrical therapy to the brain to facilitate synchronization of the two or more brain areas. The electrical therapy can be titrated to improve synchronization between the two or more areas of the brain based on the one or more signals, the synchronization between the two or more areas of the brain occurring in response to the patient being exposed to external sensory stimulus, wherein the electrical therapy does not independently cause activation of either of the two or more areas of the brain.

22 Claims, 4 Drawing Sheets

(56) References Cited

U.S. PATENT DOCUMENTS

| | | | |
|---|---|---|---|
| 7,006,872 B2 | 2/2006 | Gielen et al. | |
| 7,089,059 B1 | 8/2006 | Pless | |
| 7,120,486 B2 | 10/2006 | Leuthardt | |
| 7,171,339 B2 | 1/2007 | Repucci | |
| 7,257,439 B2 | 8/2007 | Llinas | |
| 7,280,867 B2 | 10/2007 | Osorio et al. | |
| 7,341,562 B2 | 3/2008 | Pless | |
| 7,392,079 B2 | 6/2008 | Donoghue | |
| 7,409,321 B2 | 8/2008 | Repucci | |
| 7,532,935 B2 | 5/2009 | Maschino et al. | |
| 7,577,472 B2 | 8/2009 | Li et al. | |
| 7,626,015 B2 | 12/2009 | Feinstein | |
| 7,668,591 B2 | 2/2010 | Lee et al. | |
| 7,734,340 B2 | 6/2010 | DeRidder | |
| 7,747,318 B2 | 6/2010 | John | |
| 7,801,601 B2 | 9/2010 | Maschino et al. | |
| 7,818,065 B2 | 10/2010 | Llinas | |
| 7,819,812 B2 | 10/2010 | John | |
| 7,892,182 B2 | 2/2011 | Pless | |
| 7,894,890 B2 | 2/2011 | Sun et al. | |
| 7,894,903 B2 | 2/2011 | John | |
| 7,937,138 B2 | 5/2011 | Liley | |
| 8,017,764 B2 | 9/2011 | Feinstein | |
| 8,073,534 B2 | 12/2011 | Low | |
| 8,078,281 B2 | 12/2011 | Foffani | |
| 8,090,674 B2 | 1/2012 | Ginosar | |
| 8,140,152 B2 | 3/2012 | John | |
| 2001/0003145 A1 | 6/2001 | Mori et al. | |
| 2003/0097159 A1* | 5/2003 | Schiff et al. | 607/45 |
| 2004/0073129 A1 | 4/2004 | Caldwell et al. | |
| 2004/0073273 A1 | 4/2004 | Gluckman et al. | |
| 2005/0033154 A1 | 2/2005 | deCharms | |
| 2005/0154424 A1 | 7/2005 | Tass | |
| 2005/0197560 A1 | 9/2005 | Rao et al. | |
| 2005/0209512 A1 | 9/2005 | Heruth et al. | |
| 2005/0215884 A1 | 9/2005 | Greicius et al. | |
| 2005/0283053 A1 | 12/2005 | deCharms | |
| 2006/0155348 A1 | 7/2006 | deCharms | |
| 2006/0173259 A1 | 8/2006 | Flaherty | |
| 2006/0212090 A1 | 9/2006 | Lozano et al. | |
| 2007/0067003 A1 | 3/2007 | Sanchez | |
| 2007/0123758 A1 | 5/2007 | Miesel et al. | |
| 2007/0142874 A1 | 6/2007 | John | |
| 2007/0150025 A1* | 6/2007 | Dilorenzo et al. | 607/45 |
| 2007/0191704 A1 | 8/2007 | deCharms | |
| 2007/0225674 A1 | 9/2007 | Molnar et al. | |
| 2007/0244407 A1 | 10/2007 | Osorio | |
| 2008/0001600 A1 | 1/2008 | deCharms | |
| 2008/0015459 A1 | 1/2008 | Llinas | |
| 2008/0045775 A1 | 2/2008 | Lozano | |
| 2008/0071150 A1 | 3/2008 | Miesel et al. | |
| 2008/0077039 A1 | 3/2008 | Donnett | |
| 2008/0243022 A1 | 10/2008 | Donnett | |
| 2008/0269631 A1 | 10/2008 | Denison et al. | |
| 2009/0082691 A1 | 3/2009 | Denison et al. | |
| 2009/0099623 A1 | 4/2009 | Bentwich | |
| 2009/0105521 A1 | 4/2009 | Bentwich | |
| 2009/0124919 A1 | 5/2009 | Ginosar et al. | |
| 2009/0163982 A1 | 6/2009 | deCharms | |
| 2009/0177144 A1 | 7/2009 | Masmanidis | |
| 2009/0179642 A1 | 7/2009 | deCharms | |
| 2009/0192556 A1 | 7/2009 | Wu et al. | |
| 2009/0196471 A1 | 8/2009 | Goetz | |
| 2009/0220425 A1 | 9/2009 | Moxon | |
| 2009/0318794 A1 | 12/2009 | deCharms | |
| 2009/0318826 A1 | 12/2009 | Green et al. | |
| 2010/0069739 A1 | 3/2010 | deCharms | |
| 2010/0100153 A1 | 4/2010 | Carlson | |
| 2010/0114237 A1 | 5/2010 | Giftakis et al. | |
| 2010/0121213 A1 | 5/2010 | Giftakis et al. | |
| 2010/0121214 A1 | 5/2010 | Giftakis et al. | |
| 2010/0121215 A1 | 5/2010 | Giftakis | |
| 2010/0135553 A1 | 6/2010 | Joglekar | |
| 2010/0137937 A1 | 6/2010 | John et al. | |
| 2010/0241020 A1 | 9/2010 | Zaidel et al. | |
| 2010/0262205 A1 | 10/2010 | DeRidder | |
| 2010/0280334 A1 | 11/2010 | Carlson et al. | |
| 2010/0280335 A1 | 11/2010 | Carlson et al. | |
| 2010/0280336 A1 | 11/2010 | Giftakis et al. | |
| 2010/0280403 A1 | 11/2010 | Erdogmus | |
| 2010/0286748 A1 | 11/2010 | Midani | |
| 2011/0105584 A1 | 5/2011 | Feinstein et al. | |
| 2011/0130797 A1 | 6/2011 | Talathi et al. | |
| 2011/0137371 A1 | 6/2011 | Giftakis et al. | |
| 2011/0144716 A1 | 6/2011 | Bikson et al. | |
| 2011/0184489 A1 | 7/2011 | Nicolelis et al. | |
| 2011/0196446 A1 | 8/2011 | Wu et al. | |
| 2011/0218454 A1 | 9/2011 | Low | |
| 2011/0257715 A1 | 10/2011 | Jarosh et al. | |

OTHER PUBLICATIONS

Garrett et al., The Importance of Being Variable, The Journal of Neuroscience, Mar. 23, 2011, 31(12): 4496-4503.

Keimel et al., "Development Proposal: A Low Cost System for fMRI and Spectroscopic Screening and Monitoring of Alzheimer's Disease", Advanced Function Biomedical Imaging, University of Minnesota, Fall 2008, Dec. 12, 2008.

Lynall et al., "Functional Connectivity and Brain Networks in Schizophrenia", J. Neuroscience, Jul. 14, 2010—30(28):9477-9487.

Pihlajamaki et al., "Functional MRI Assessment of Task-Induced Deactivation of the Default Mode Network in Alzheimer's Disease and At-Risk Older Individuals," Behavioral Neurology 21 (1) (2009) 77-91.

Sperling, et al., "Functional Alterations in Memory Networks in Early Alzheimer's Disease" Neuromol Med (2010) 12:27-43.

Van Veen, et at, "Localization of Brain Electrical Activity via Linearly Constrained Minimum Variance Spatial Filtering" IEEE Transactions on Biomedical Engineering, vol. 44, No. 9, Sep. 1997.

Westlye, et al.., "Increased Hippocampal Default Mode Synchronization During Rest in Middle-Aged and Elderly APOE ε4 Carriers: Relationships with Memory Performance," The Journal of Neuroscience, May 25, 2011, 31(21): 7775-7783.

Loddenkkemper, et al., "Circadian Patterns of Pediatric Seizures," Neurology 76, Jan. 11, 2011: 145-153.

* cited by examiner

ELECTRICAL THERAPY FOR FACILITATING INTER-AREA BRAIN SYNCHRONIZATION

PRIORITY

This application claims the benefit of U.S. Provisional Application No. 61/477,346 filed on Apr. 20, 2012, the entire contents of which are incorporated herein by reference.

TECHNICAL FIELD

The disclosure relates to medical systems, and, more particularly, medical systems that deliver a therapy to facilitate synchronization between two or more brain areas.

BACKGROUND

Implantable medical devices, such as electrical stimulation devices, may be used in different therapeutic applications, such as for deep brain stimulation, spinal cord stimulation, pelvic stimulation, gastric stimulation, peripheral nerve stimulation, or functional electrical stimulation of a target tissue site within a patient. An electrical stimulation device may be used to treat a variety of symptoms or conditions of a patient, such as chronic pain, tremor, Alzheimer's disease, Parkinson's disease, other types of movement disorders, seizure disorders (e.g., epilepsy), urinary or fecal incontinence, sexual dysfunction, obesity, mood disorders, gastroparesis, or diabetes. In some therapy systems, an implantable electrical stimulator delivers electrical therapy to a target, tissue site within a patient with the aid of one or more electrodes, which may be deployed by medical leads.

SUMMARY

In general, the disclosure relates to methods, systems, and devices for characterizing synchronization between two or more areas of the brain and titrating a therapy to facilitate synchronization between the two or more areas.

Various embodiments concern a method of treating a condition of a brain of a patient, the method comprising: delivering an electrical therapy to the brain of the patient; monitoring one or more signals indicative of synchronization between two or more areas of the brain; and titrating the electrical therapy to improve synchronization between the two or more areas of the brain based on the one or more signals, the synchronization between the two or more areas of the brain occurring in response to an external sensory stimulus, wherein the electrical therapy does not independently cause activation of either of the two or more areas of the brain, and wherein delivering, monitoring, and titrating are performed at least in part by control circuitry of a medical device. Method embodiments may further comprise controlling exposure of the patient to the external sensory stimulus. In such embodiments, the external sensory stimulus comprises at least two different types of associated stimulus; and the two or more areas of the brain are respectively associated with brain functions for processing the at least two different types of associated stimulus. In such embodiments, the external sensory stimulus comprises video and associated sounds of activity in the video; and the two or more areas of the brain are respectively associated with brain functions for processing sight and sound.

In various embodiments, the external sensory stimulus that causes the synchronization between the two or more areas of the brain comprises only a single stimulus, the external sensory stimulus that causes the synchronization between the two or more areas of the brain comprises a sensory-motor stimulus, and/or monitoring the one or more signals comprises determining a measure of synchronization between the two or more areas of the brain based on two or more signals respectively generated by the two or more areas of the brain and the measure of synchronization measures consistency in the difference between one or both of the frequencies and phases of a first signal from one of the two or more areas of the brain and a second signal from another of the two or more areas of the brain.

In various embodiments, the electrical therapy comprises a low frequency electrical carrier signal that facilitates synchronization between the two or more areas of the brain, the electrical therapy is delivered at a beta or a gamma frequency range, the electrical therapy is delivered using only two electrodes, the two electrodes respectively functioning as an anode and a cathode, and/or the electrical therapy is delivered by one or more electrodes implanted within the brain proximate to the thalamus.

Various embodiments include sensing at least one signal using external sensors while the patient is exposed to one or more sensory events; and determining the degree of synchronization between the two or more areas of the brain based on the at least one signal, wherein delivering the electrical therapy, monitoring, and titrating are performed only if the two or more areas of the brain are determined to be relatively unsynchronized.

Various embodiments concern a system comprising: one or more sensors configured to receive one or more signals indicative of brain activity; a stimulation generator configured to deliver electrical therapy to the brain of a patient; and control circuitry comprising a processor and memory having program instructions executable by the processor, the control circuitry configured to determine a measure of synchronization between two or more areas of the brain of the patient and titrate delivery of the electrical therapy to improve synchronization between the two or more areas of the brain, wherein the electrical therapy is titrated by the control circuitry such that synchronization between the two or more areas of the brain occurs in response to external sensory stimulus and the electrical therapy does not independently cause activation of either of the two or more areas of the brain. In such embodiments, the control circuitry may be configured to titrate the electrical therapy based on the measure of synchronization, the measure of synchronization may measure consistency in the difference between the phases of a first signal from one of the two or more areas of the brain and a second signal from another of the two or more areas of the brain. In various implementations of the above embodiments, the measure of synchronization measures frequency similarity between a first signal from one of the two or more areas of the brain and a second signal from another of the two or more areas of the brain.

In various implementations, the electrical therapy comprises a low frequency electrical carrier signal that facilitates synchronization between the two or more areas of the brain and/or the stimulation generator is configured to deliver the electrical therapy within one or both of a beta frequency range and a gamma frequency range.

In various implementations, the system further comprises a user interface, wherein the control circuitry is configured to initiate exposure of the external sensory stimuli to the patient on a user interface. In various implementations of the above embodiments, at least one of the two or more areas of the brain is associated with a brain function for processing the one or more external sensory stimuli to which the patient is exposed. In various implementations of the above embodiments, the control circuitry is distributed between two or more physically separate devices.

Various embodiments concern a system, comprising: means for delivering an electrical therapy to a brain of a patient; means for monitoring one or more signals indicative of synchronization between two or more areas of the brain; and means for titrating the electrical therapy to improve synchronization between the two or more areas of the brain based on the one or more signals, wherein the electrical therapy is titrated such that the synchronization between the two or more areas of the brain occurs in response to external sensory stimulus and the electrical therapy does not independently cause activation of either of the two or more areas of the brain.

Various embodiments concern a physically embodied computer-readable medium comprising instructions executable by a processor to cause a medical device to: deliver an electrical therapy to a brain of a patient; monitor one or more signals indicative of synchronization between two or more areas of the brain; and titrate the electrical therapy to improve synchronization between the two or more areas of the brain based on the one or more signals, wherein the electrical therapy is titrated such that the synchronization between the two or more areas of the brain occurs in response to external sensory stimulus and the electrical therapy does not independently cause activation of either of the two or more areas of the brain.

The details of various examples are set forth in the accompanying drawings and the description below. Other features, objects, and advantages will be apparent from the description and drawings, and from the claims.

DETAILED DESCRIPTION

Figure 1:
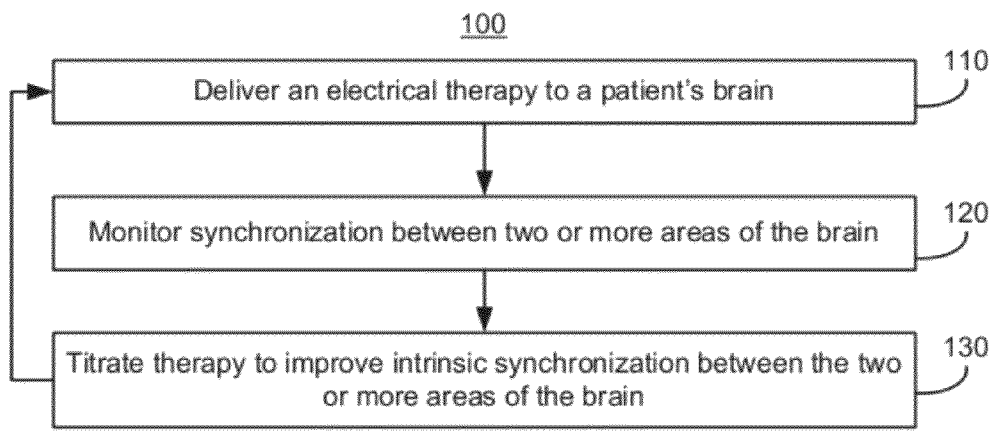
FIG. 1 is a flow diagram for titrating a therapy to improve synchronization within a patient's brain.

The methods and apparatuses described herein provide for monitoring synchronization of two or more brain areas and/or treating a brain condition by facilitating synchronization of the two or more brain areas.

The human brain is composed of billions of neurons interconnected and organized into various areas to perform a variety of functions. The neurons of a particular area can be associated with one or more brain functions. These areas can share networks of neurons. Electrical activation of neurons is the basis for function of brain areas and communication amongst the various brain areas along these networks. It is generally thought that the activation of numerous neurons is necessary to carryout each brain function. Moreover, for various areas of the brain, many of the neurons in an area of the brain will depolarize in synchrony in an effort to carryout a function supported by the area. One measure of the level of engagement of an area of the brain is the regularity of the bioelectrical oscillations of the neurons in the area. The oscillation of the electrical activity of the brain areas can be measured as a bioelectrical brain signal, such as a local field potential (LFP) or electroencephalogram (EEG) signal.

Various areas of the brain communicate with one another to coordinate activities and ultimately carryout the multifunctional abilities of the brain. For example, if a person is counting out loud, a cortical area of the brain associated with higher level thought (e.g., mathematical abilities) may be activated in some synchronous way with Broca's area of the brain which is associated with speech abilities. For some areas of the brain, the bioelectrical oscillations of the different areas will correspond in some way when the functions of these different areas of the brain are being coordinated. For example, if a subject is witnessing another person speaking, then the two areas of the subject's brain respectively associated with sound perception (i.e. temporal lobe) and visual perception (i.e. visual cortex) may have synchronous bioelectrical activity. In this example, the frequency of bioelectrical oscillation of the temporal lobe may closely match the bioelectrical oscillation of the visual cortex and/or the periods of their respective oscillations may have a fixed relationship (e.g., consistently off by a quarter of a period).

Certain neurological and psychiatric disorders (for example, autism, schizophrenia, and Alzheimer's disease) can be characterized by deficits in large-scale integration across distributed brain networks. This unlinking of brain networks ultimately gives rise to cognitive deficits. Inter-area informational connections can become weak or break down, leading to deficits in the coordination of distributed processes among these areas. This reduced coordination may allow activities in one brain area to occur more independently relative to other areas.

Schizophrenia and various other brain conditions can be characterized by inadequate or non-existent synchronization between different brain areas. Schizophrenia can further be characterized by errant brain activity that does not correspond with sensory input. For example, a person suffering from schizophrenia may erroneously perceive to hear voices despite the voice sound not actually existing. The erroneous perception of the voice may originate in one area of the brain but because of lack of coordination between various brain areas the brain may fail to override the erroneous perception (e.g., where failure to recognize a person speaking via the auditory and/or visual perception areas might have overridden the erroneous perception of the voice in a normally functioning brain). Synchronization of brain areas can allow brain areas to coordinate their functions and corroborate or contradict activities (e.g., hearing a sound) of another area as a type of quality control check. Lack of proper synchronization may inhibit these quality control checks and other abilities in some disease states.

Various embodiments of the present disclosure concern controlling delivery of an electrical therapy to the brain to improve synchronization to address schizophrenia, autism. Alzheimer's disease, and/or other brain conditions that can be characterized by inadequate or nonexistent coordination between brain areas. Neurostimulation to facilitate resynchronization of brain areas may reverse cognitive effects associated with neurological disorders caused by desynchrony.

FIG. 1 illustrates a flow chart of a method 100 for controlling an electrical therapy to improve synchronization of bioelectrical activity between two or more areas of a brain. The method 100 includes delivering 110 an electrical therapy to a patient's brain. The electrical therapy may be delivered 110 in the manner of deep brain stimulation, which is discussed further herein. By way of example, the electrical therapy may be a continuous signal or series of pulses delivered 110 using one, two, or more electrodes implanted in the brain proximate the thalamus or other area. Electrical therapy may be delivered 110 continuously (e.g., for 24 hours or longer) or intermittently. The brain activity of one or more areas of the brain is monitored 120. Monitoring 120 may be started before, concurrent with, or after electrical therapy delivery 110, and may be continuous or intermittent. Monitoring 120 can include receiving one or more signals from the brain, such as EEG, LFP, ECoG, MEG, and/or fMRI signal, and analyzing the one or more signals to characterize synchronization of bioelectrical activity between the brain areas. For example, two EEG signals respectively associated with different areas of the brain may indicate that the two brain areas are to some degree synchronized based on a parameter of the two EEG signals, such as both signals having significant frequency components at the same or close frequencies or temporal correlation of burst activity in the signals, for example. In various embodiments, monitoring 120 may concern receiving one signal indicative of synchronization of the two or more areas, synchronization characterized by a biomarker in the signal and/or other aspect of the signal such as frequency content (e.g., increased power at a certain frequency or frequency band in the frequency domain).

The electrical therapy can be titrated 130 to improve intrinsic synchronization between the two or more areas of the brain. The term "intrinsic synchronization," as used herein, refers to synchronization between areas of the brain in response to appropriate triggers, such as an external sensory stimulus (e.g., exposure to a video of a person talking). The electrical therapy should not independently cause synchronization between areas of the brain, nor should the electrical therapy independently cause activation of one or more areas of the brain such that the patient experiences artificially induced sensory perceptions (e.g., the patient perceives to hear sounds or see flashes of light that do not actually exist), and such synchronizations/activations are not intrinsic. Preferably, the electrical therapy is titrated 130 such that two or more areas of the brain synchronize in some manner in response to external sensory input or action of the patient that is associated with the two or more areas of the brain that synchronize. In this way, the two or more particular areas of the brain would not show the same synchronization, or any synchronization during therapy delivery 110, but for when some sort of external sensory input is present.

The electrical therapy can be in the form of a carrier wave signal, such as a low frequency carrier wave signal in the beta frequency range or high frequency carrier wave signal in the gamma frequency range. In this way, the electrical therapy can function by providing a base level of energy that can make it easier for different brain areas to effectively communicate as indicated by intrinsic synchronization.

Titration 130 can include changing one or more parameters of the electrical therapy. Titration 130 can include changing the energy level of the electrical therapy, such as by adjusting frequency, amplitude, and/or duration of the electrical therapy.

Although many targets for facilitating synchronization are contemplated, the brainstem area, reticular formation, and the thalamus are areas of particular interest for delivering neurostimulation because of their diffuse projections within the brain. Stimulation energy delivered directly to these areas has the potential to branch out to other areas targeted for improvement in synchronization. Similar targets with ascending activation abilities are also contemplated as areas for delivering stimulation.

Titrating an electrical therapy to improve synchronization can include any increase in synchronization between two or more targeted brain areas, such as where little or no synchronization was observed before therapy delivery and a greater amount or at least a little amount of synchronization is observed in association with the delivery of the electrical therapy and the presence of external stimuli. In such a case, increased synchronization (e.g., in terms of intensity, duration, and/or frequency of episodes) can be used to titrate the electrical therapy, where the increased synchronization indicates more effective electrical therapy parameters relative to previous parameters or no therapy. Likewise, decreased synchronization can be used to titrate the electrical therapy, where the decreased synchronization indicates less effective electrical therapy parameters relative to previous parameters. In this way, electrical therapy parameters can be changed to improve synchronization of brain areas.

Figure 2:
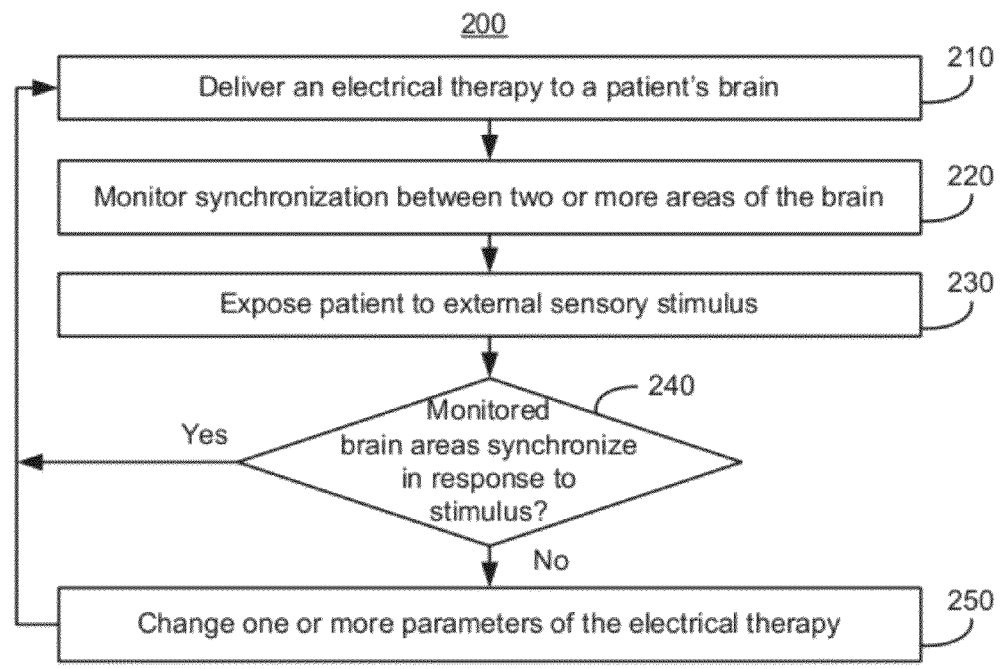
FIG. 2 is a flow diagram for controlling a therapy to improve synchronization within a patient's brain.

FIG. 2 illustrates a flow chart of a method 200 for controlling an electrical therapy to improve synchronization of bioelectrical activity between two or more areas of a brain. The method 200 includes delivering 210 an electrical therapy to a patient's brain and monitoring 220 synchronization between two or more areas of the brain, both of which can be done in accordance with any technique disclosed herein.

During electrical therapy delivery 210 and monitoring 220, the patient can be exposed 230 to an external sensory stimulus. Such an external sensory stimulus can be a picture, music, application of a cold compress to skin, a suggestion to think about something specific, and/or other controlled introduction of sensory input, for example. The stimulus is "external sensory" in the sense that it comes to the brain by way of a sensory organ (e.g., eyes and/or ears) being sensed in the normal course and is not induced by artificial electrical stimulation itself.

Exposure 230 to sensory stimulus can be useful because the electrical therapy is a sub-threshold therapy that facilitates proper brain function but does not drive activation of brain areas itself. Delivery 210 of the electrical therapy to the brain of a patient who has a condition inhibiting coordination of different brain areas can help these areas coordinate (e.g., synchronize in activity) when it would be expected that the areas would coordinate (e.g., in response to external sensory stimulus). The external sensory stimulus can test 240 whether the electrical therapy effectively supports the coordination of the brain areas associated with processing the external sensory stimulus, where such coordination of the brain areas would normally be expected in processing the external sensory stimulus if the patient did not have a brain condition.

Introducing external sensory stimulus can take the form of presenting a patient with a situation, such as asking a patient to move a block around a table in a particular manner. In this case, the motor areas of the brain may be expected to evidence coordination by correspondence in bioelectrical activity with areas of the brain associated with processing tactile, motor feedback (e.g., object weight or inertia) and/or visual input. In a healthy individual or with a individual receiving effective electrical therapy, the bioelectrical oscillations of the motor area of the brain may correspond in some manner to the bioelectrical oscillations of one or more areas of the brain that support tactile, feedback, and/or visual sensory perception as the patient moves the object. Frequency matching between the dominant frequency components of the signals from the two or more areas in the frequency domain may indicate synchronization (dominance measured by power or other energy parameter). Phase locking between oscillating patterns of the signals may be another parameter indicative of synchronization between the brain areas.

In the method 200 of FIG. 2, one or more parameters of the electrical therapy can be changed 250 if the test 240 determines that the monitored 220 areas do not synchronize in response to the external sensory stimulus. This may be indicted by the motor area and tactile, feedback, and/or visual sensory perception areas of the brain tailing to show any bioelectrical changes indicative of synchronization, which may be corroborated by the patient having difficulty in moving the object as intended. In some embodiments, the test 240 will measure the degree of bioelectrical synchronization between the areas and compare the measure to a predetermined threshold, the predetermined threshold representing a satisfactory degree of synchronization between the areas. The predetermined threshold can be a default setting based on clinical or population data, or can be customized and set by a clinician for the patient.

If the test 240 determines that the monitored 220 brain areas do not synchronize in response to the external sensory stimulus (e.g., insufficient synchronization activity is sensed as determined by the degree of synchronization being below the predetermined threshold) then one or more of the electrical therapy parameters is changed 250. Such a change 250 in parameter may be, for example, an increase or decrease in frequency, amplitude, waveform, and/or pulse characteristic (e.g., pulse width or other shape characteristic). The method 200 can then loop back to delivering 210 the electrical therapy. It is noted that the electrical therapy may be delivered 210 continuously or intermittently during each step of the method 200, including during changing 250 of parameters. Likewise, monitoring 220 may be continuously or intermittently performed.

If the test 240 determines that the monitored 220 brain areas do synchronize in response to the external sensory stimulus (e.g., changes in the bioelectrical signals indicate sufficient synchronization activity as indicated by comparison of a measure of synchronization to the predetermined threshold) then the method 200 loops back to delivery 210 of the electrical therapy without a parameter change.

If the test 240 determines that the monitored brain areas do not synchronize in response to the external sensory stimulus because at least one of the two or more areas of the brain was already activated before exposure 230 of the patient to the external sensory stimulus and/or the two brain areas were already synchronized, this could indicate that the electrical therapy is improperly driving activation of one or more areas of the brain. In this case, the change 250 could be a decrease in one or more energy parameters, such as lowering of amplitude, frequency, duration, and/or change in a pulse characteristic (e.g., pulse width or other shape characteristic). In this way, delivery 210 of the electrical therapy can be titrated based on monitoring 220 and testing the brain's response under various conditions. It is noted that some bioelectrical activity of the brain areas may commonly be synchronized, such as two or more brain areas having similar low level beta frequency range content, regardless of external sensory stimuli. Continuous synchronous bioelectrical activity before and after introduction of the stimuli is not considered synchronization in response to the stimulus. However, if the continuous synchronous bioelectrical activity increased in amplitude in the time domain or power in the frequency domain in correlation with introduction of the sensory stimulus, then such a change can indicate synchronization.

Titration of an electrical therapy, as referred to herein, is to be performed in a manner so that the electrical therapy does not independently cause activation of either of the two or more brain areas having insufficient synchronization but does improve intrinsic synchronization between the areas. Independent activation in this sense does not refer to depolarization of one or a few neurons, but rather large scale depolarization of neurons organized in an area of the brain for performing some function. It is contemplated that the delivery of electrical stimulation to the brain will depolarize some neurons, but the depolarization of a few neurons does not constitute activation of an area of the brain unless some function associated with the brain area is expressed through the depolarization or large scale organization of the neurons is caused by the electrical stimulation. Too much electrical stimulation (e.g., excessive energy level of a therapy) can cause certain areas of the brain to activate and produce perceptions or thoughts associated with the functions of the artificially activated brain areas, referred to herein as driven brain network activation. In such a case, the activation of the network of the brain area is driven by the electrical stimulation. Driven activation of brain network through electrical stimulation may be appropriate for some therapeutic applications outside of the scope of the present disclosure. However, the stimulation of the present disclosure concerns stimulation below a threshold that would give rise to excessive large-scale synchrony in distributed brain areas, which in some cases could lead to induction of an epileptic state. It is intended that the present electrical therapy be titrated below this energy level so that the electrical stimulation does not independently cause any of the areas of the brain characterized by insufficient synchronization activity to be activated in this way, and further that such activations only occur intrinsically (i.e. in response to external sensory stimuli or other normal trigger for activation of the brain area and associated function). The flow chart of the method 300 of FIG. 3 further demonstrates titration in this manner, among other things.

Figure 3:
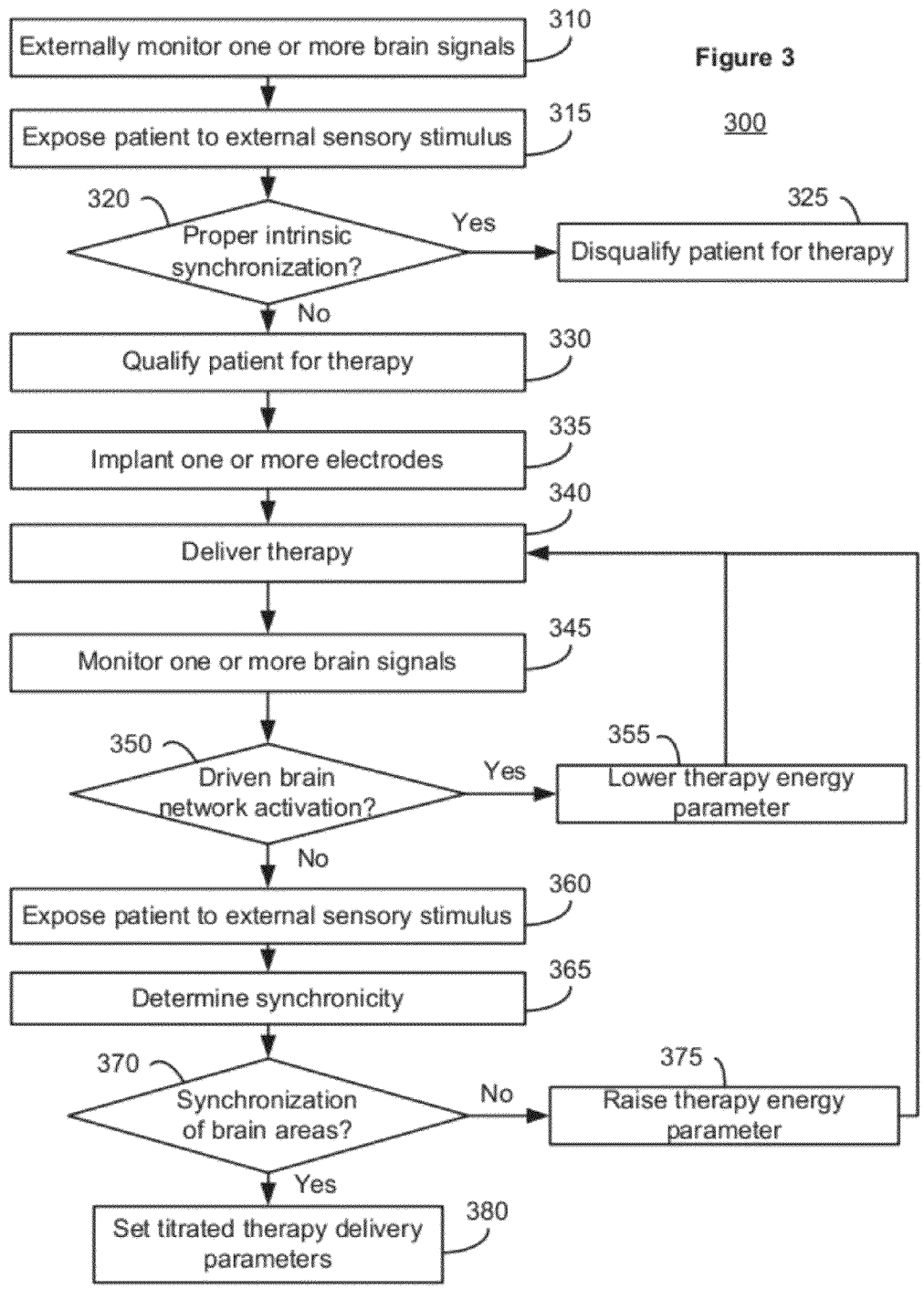
FIG. 3 is a flow diagram demonstrating various aspects of providing a therapy for improving synchronization within a patient's brain.

FIG. 3 illustrates a flow chart of a method 300 for controlling an electrical therapy to improve synchronization of bioelectrical activity between two or more areas of a brain. Among other things, the method 300 demonstrates how a patient may be evaluated for qualification of the electrical therapy for synchronization. The method 300 includes externally monitoring 310 one or more brain signals. Such external monitoring 310 can be performed by sensing one or more EEG signals with electrodes placed on the head of a patient. The external monitoring 310 can test 320 what, if any, areas of the brain are synchronizing without any therapeutic intervention. The patient may be exposed 315 to an external sensory stimulus, as discussed elsewhere herein, such as a video of a person talking or a sensory-motor test (e.g., moving an object or walking up stairs). If the test 320 indicates that the patient's brain does properly synchronize in response to appropriate sensory triggers, then the patient may be disqualified 325 for therapy. However, if proper intrinsic synchronization of the brain in response to an external sensory stimulus is not identified as determined by test 320, then the patient can be qualified 330 for therapy.

While in some embodiments test 320 may look for any kind of synchronization, other embodiments may test 320 only for specific types of synchronization. For example, the test 320 may only concern the type of synchronization that would be expected from the external sensory stimulus used in the exposure 315. In various embodiments, if the external sensory stimulus was presentation of a fresh flower, then the brain areas associated with processing sight and smell may be specifically monitored 310 to determine whether synchronization between these areas can be identified, and only synchronization of these brain areas can pass the test 320 for therapy disqualification 325. Other areas of the brain can likewise be selectively tested.

One or more electrodes can be implanted 335 in the brain based on the patient being qualified 330 for therapy. As further discussed herein, the one or more electrodes can be implanted on the surface of the brain or deeper within the brain on one or more leads. Electrical therapy may be delivered 340 using the one or more implanted 335 electrodes. Monitoring 345 of one or more brain signals may be performed using one or more of the implanted 335 electrodes and/or one or more of the electrodes used for external monitoring 310. The one or more brain signals can be used to test 350 whether brain network activity of the monitored areas is driven by the therapy. If test 350 determines that the therapy is driving brain network activation, such as by identifying significant bioelectrical activity irrespective of sensory input, patient state, or other factor in the one or more brain areas, then a therapy energy parameter can be lowered 355 (e.g., lowering amplitude, pulse width, pulse frequency) and the titrating loop 355-340-345-350 can be tried again. A therapy energy parameter can be any delivery parameter of the therapy that influences neural activity, including frequency, amplitude, and/or pulse characteristics such as width and shape.

It may be preferable to minimize sensory input when performing the monitoring 345 and test 350 because brain areas could activate intrinsically in response to sensory input. In various circumstances, it is preferable to isolate the therapy as the independent cause of brain activation when trying to determine whether the therapy drives brain network activation. It may be determined that the electrical therapy is driving brain activation if brain activation of sensory areas are identified despite lack of sensory input, irregular activation, and/or sustained or unduly prolonged activation of brain areas uncharacteristic of intrinsic brain activity, such as divergence from established signal baselines indicative of brain area activation.

In addition to determining whether the electrical therapy is too aggressive by testing 350 driven brain network activation, the method 300 can include determining whether the therapy is aggressive enough to meaningfully address inadequate brain synchronization. To this end, the method 300 includes exposing 360 the patient to an external sensory stimulus, which can be done in any manner referenced herein. A determination of synchronicity 365 can be made based on the external sensory stimulus exposure 360 and the one or more monitored 345 brain signals. The determination of synchronicity 365 can concern any metric referenced herein for characterizing the degree of synchronization between two or more areas of the brain. In various embodiments, a number system can be used to represent the synchronicity between two or more brain areas, such as an indexed scoring system. For example, a metric for characterizing synchronization, such as % match (e.g., correlation of signal features or correlation between raw signals), can be calculated for two or more signals respectively associated with two or more brain areas. A certain % match range can be given one indexed score (e.g., 0-20% is indexed for a score of 1, 21-40% is indexed for a score of 2, and so on in equivalent increments).

If test 370 determines that areas of the brain are showing sufficient signs of synchronization based on the determination of synchronicity 365 (e.g., surpassing a threshold or within a range of a scoring or other index), then the titrated therapy delivery parameters (e.g., the current parameters that passed both tests 350 and 370) can be set as delivery parameters. If test 370 determines that areas of the brain are showing insufficient signs of synchronization and/or no improvement from previous tests, then a therapy energy parameter can be raised 375 (e.g., increasing amplitude, pulse width, pulse frequency) and the titrating loop 375-340-345-350-360-365-370 can be tried again. Although the flow chart of FIG. 3 illustrates that the method 300 returns to testing 350 when the electrical therapy drives brain network activation, other options are contemplated. For example, if test 370 determines that areas of the brain are showing insufficient signs of synchronization and/or no improvement from previous parameters, then one or more therapy energy parameters can be raised 375 and the method can next advance to exposing 360 the patient to the external sensory stimulus or determining synchronicity 365 (in the latter case the exposure 360 may be ongoing but various embodiments are not so limited).

As such, the techniques of the method 300 of FIG. 3 can scan therapy energy parameters up and down to identify appropriate parameters that provide for efficacious stimulation while avoiding inappropriate stimulation. While method 300 discusses changing therapy energy parameters, it is contemplated that other therapy changes can optionally be made in the same manner. For example, an electrode on a lead may be advanced or retracted within the brain based on the tests 350 and 370 for driven brain network activation and synchronicity, until an optimal electrode position is found that provides for efficacious stimulation while avoiding inappropriate stimulation. The electrode or electrode combination used for delivering therapy can also be changed. In this way, one electrode combination or position may cause driven brain network activation or not improve synchronization of one or more brain areas, and in which case the electrode position can changed by advancing or retracting a lead or a different electrode combination can be used for electrical therapy delivery until satisfactory synchronization results are observed as discussed herein.

Various embodiments can collect and store historical values and outcomes from tests 350 and 370 in memory, such that it is unnecessary to scan in certain ranges when it can be recognized (e.g., by a processor of control circuitry) that a parameter configuration, or one close to it, has already been tested 350 and 370. Such automatic recognition can be useful so that a parameter scan does not return to a configuration already tested. For example, if a previous test 350 indicated that stimulation at 5 volts caused driven brain network activation, and the voltage was later being scanned upward looking to identify a voltage level that does cause sufficient signs of synchronization and/or improvement, the scanning up in voltage can be stopped before it reaches, or approaches, the 5 volt level, to avoid further driving brain activity. In such a case, a different parameter may be changed than the one already used in the scan, such as frequency and/or electrode combination, either automatically or manually.

When delivery parameters are found that pass both tests 350 and 370 by facilitating synchronization of brain areas while not driving brain network activation, therapy delivery parameters can be set 380 based on which delivery parameters passed both 350 and 370. Setting 380 therapy delivery parameters can include programming (e.g., saving delivery parameters in memory) an implantable medical device for long term delivery using the therapy parameters.

Various embodiments may pertain to delivering a therapy to address a cognitive disorder characterized by deficits in memory and/or concentration, such as mild cognitive impairment and Alzheimer's disease. For example, the method 300 of FIG. 3 (or any other method or embodiment disclosed herein) could be specifically directed to such conditions. In the case of FIG. 3 in particular, the external sensory stimulus to which the patient is exposed 360 could pertain to a memory or cognitive task, such as asking the patient to recall something from memory, count, or assemble a puzzle. The brain areas for which inadequate synchronization is identified could be brain areas that support memory or other cognitive functions. As such, electrical stimulation can be set 380 for facilitating synchronization between brain areas that support cognitive function. Such brain areas may include hippocampal and/or thalamic structures, however other brain areas may be additionally or alternatively targeted.

Controlled exposure of a patient to an external sensory stimulus, such as in FIGS. 2 and 3, may not be needed in all cases because brain signal monitoring may evidence synchronization, or lack thereof without purposefully directing the patient's attention to an external sensory stimulus. However, controlled exposure of the patient to an external sensory stimulus can be particularly useful in some circumstances. Controlling the attention of a patient by deliberate exposure to a predominant sensory experience (e.g., watching a video) allows monitoring to focus on brain areas expected to respond to those predominant sensory experiences while assuming other sensory inputs are, at least temporarily, drowned out. For example, if a video of a person speaking was shown to the patient, then the areas of the brain expected to show synchronous activity can be those areas associated with processing sight and sound, and perhaps further a speech processing area of a brain. This can simplify monitoring and patient assessment because some areas of the brain might synchronize under appropriate conditions while other areas might not. As such, controlled exposure of the patient to an external sensory stimulus allows selective isolation of brain areas of interest. Furthermore, in cases where it is difficult to discriminate data from one area of the brain and data from another area of the brain from the noise of all other areas of the brain, then controlled exposure can take the burden off discriminating signals from different brain areas where new synchronous activity (i.e. changes in bioelectrical synchronization indicating increased synchronicity) or lack thereof can facilitate conclusions regarding correlation between therapy delivery and the introduction of an external sensory stimulus.

Stimulus in a controlled setting can include physical therapy, talk therapy (i.e. psychotherapy), a memory task, a cognitive task, occupational therapy, and exposure to controlled situations, for example. In some cases, a stimulus can be a sensory-motor stimulus, such as having a patient move an object around a table in a way that engages both motor and sensory feedback areas of a patient's brain. The two or more areas of the brain being monitored for synchronous bioelectrical activity can be areas that handle motor skills and sensory feedback.

Controlled exposure can also help obtain baseline brain information for use in identifying synchronization of areas of the brain. For example, minimizing brain activation by minimizing sensory input can help brain signal monitoring to characterize the brain areas in their idle states to obtain baseline measures of non-synchronized bioelectrical brain activity. Brain activity, including synchronous brain activation, may be minimal when sensory inputs are minimized and the patient is calm, and such minimal brain signal activity can be used to form a baseline for a later comparison of signal data acquired in connection with exposure of an external sensory stimulus. A patient can be calmed and sights, sounds, and disruptions that could activate brain networks associated with processing these external events can be minimized during testing prior to and during the controlled exposure. As such, controlled exposure to stimulus can help isolate the differences in signals between non-activated brain areas and activated and/or synchronized brain areas.

In some cases, the patient is exposed to external sensory stimuli by being confronted with real world situations, such as by walking down a street. A brain may be monitored as discussed herein to identify and measure synchronization indicators that can result from such environmental external sensory stimuli. For example, without controlling external sensory stimuli, it can be assumed that a patient will encounter such stimuli over time in real world settings. If sufficient indicators of synchronization are identified as the patient goes about his or her usual activities (e.g., number of synchronization episodes per day or percentage of time exhibiting an indicator of synchronization) then this can indicate that the therapy is successful, whereas a lack of identified synchronization events (e.g., below a threshold number or percentage of time) may trigger a therapy parameter to be changed manually or automatically to titrate the therapy. In various embodiments, control circuitry may monitor for indicators of synchronization of brain areas, and if an insufficient amount of indicators are sensed (e.g., number of synchronization events per hour or day being a threshold, or time spent in a synchronized state per hour or day being below a threshold), then therapy delivery to facilitate synchronization can be triggered, titrated, or otherwise changed (e.g., initiated or increased in intensity). Monitoring can then continue and the therapy delivery may be paused or adjusted downward when a sufficient amount of indicators are sensed (e.g., rise back above the threshold).

In various embodiments, use of a controlled exposure to external sensory stimulus or other test may be used to validate purposeful synchronization between two or more brain areas. For example, controlled exposure may be used to account for the chance that synchronization between two or more areas is incidental, minor, or non-coordinated synchronization (i.e. it coincidental and not the result of coordination). As such, isolating the external sensory stimulus as a variable can provide some evidence that brain areas associated with processing the type of stimulus introduced are indeed synchronizing in response to the exposure, and are not synchronized merely coincidentally.

In various embodiments, the external sensory stimulus to which the patient is exposed is different between various exposure episodes. The type of external sensory stimulus can be changed between exposures to test different types of brain areas that would be expected to synchronize in response to the various different external sensory stimuli. For example, a first exposure can be a video testing sight and sound processing areas of the brain, a second exposure can be handing the patient a flower to test smell and tactile processing areas of the brain, and a third can include having the patient perform some physical task. In some patients, some areas of the brain may be found to appropriately synchronize in response to external sensory stimulus while some other areas may not. In such cases, therapy decisions, including selecting therapy targets, positioning therapy delivery electrodes, selecting electrodes and electrode combinations, and titrating therapy parameters, can be made on the basis of which of multiple exposures of different types of external sensory stimuli caused synchronization of which brain areas, such that the therapy is targeted to those areas of the brain evidencing lack of coordination with other areas.

In various implementations, the patient is not exposed to external sensory stimulus in a controlled manner. It is contemplated that a patient will experience exposure to external sensory stimulus in the everyday life of the patient. Two or more brain areas can be monitored for synchronous activity and a therapy titrated based on increasing synchronization (e.g., increased intensity, duration, and/or frequency of episodes of synchronization), wherein the increased synchronization indicates more effective electrical therapy parameters relative to previous parameters or no therapy. As such, controlled exposure is not required in all cases and exposure to external sensory stimuli includes environmental interaction.

In various embodiments, the brain is continuously monitored for synchronous activity. All signal data may be saved, or only selected portions corresponding to identification of synchronous activity may be saved, in some embodiments. Such chronic monitoring may be performed by a wearable external sensing device and/or an implantable medical device. However, in some embodiments, monitoring brain areas and identifying synchronization may only occur in connection with specific testing periods, such as in connection to controlled exposure to external sensory stimuli. For example, monitoring may only be performed in a clinical setting. Monitoring by a wearable or implantable device may be automated in coordination with an external programmer, which may initiate monitoring when a patient is presented with sensory stimulus on the screen of the external programmer or some other external device. Such monitoring and testing may be scheduled to be performed periodically by a device.

A synchronization threshold can be developed for a particular patient. The synchronization threshold can be used to determine when two or more areas of the brain are sufficiently synchronized, such as by a processor of controller circuitry. In various embodiments, when a patient is exposed to an external sensory stimulus, the processor can analyze what level of increase in synchronization was detected between the brain areas (e.g., dominant oscillatory frequencies go from 10 Hz difference to 2 Hz difference) and set that amount, or a lesser amount (e.g., half or two thirds of that amount), as a synchronization threshold or otherwise identify synchronization based on the observed increase. Determining a synchronization threshold can be useful when two or more brain areas typically have low intensity and/or intermittent synchronization even when the patient is not actively using the functions associated with those areas. However, the brain areas may then have a large increase in synchronization when the patient is exposed to an external sensory stimulus. The increase may be quantized (e.g., percent frequency matching or percent increase in power level of matching frequencies) and then a point selected within the increase. For example, if there is usually about a 10% neural activity match between two brain areas when the patient is clearly not using certain brain functions common to two or more areas, and the degree of synchronization increases to 40% when the patient is exposed to the external sensory stimulus, then the synchronization threshold can be set within this range, such as ⅓ (20%) or ¼ (25%) of the range. Synchronization thresholds for other parameters can likewise be set, such as for amplitude, frequency, frequency band power, and phase of bioelectrical brain signals, among others. In some embodiments, indicators of synchrony must be paired in some manner to be considered indicative of synchrony. For example, an increase in signal amplitude of two signals from two brain areas may also require similarity in frequency content (e.g., both having elevated power levels at a certain frequency or in a frequency range) between the two signals to be considered indicative of synchronization and for recognition of an episode of synchronization.

It is noted that a person with a brain condition that inhibits synchronization of brain areas may still have periods of synchronization, or some degree of synchronization. The synchronization may be short lived, infrequent, and/or weak depending on the degree and nature of degradation of the connections between networks. As such, various embodiments concern extended monitoring and tracking synchronization to determine whether the episodes are becoming less frequent (e.g., episodes per hour, day, week), shorter, and/or weaker (e.g., lesser frequency content correlation or other correlation in electrical activity between the areas). Such measures may be used for tracking of a condition and/or titrating a therapy. Also, the use of a minimum synchronization duration threshold may be used to qualify an episode of synchronization for identification, tracking of a condition, and/or controlling a therapy. In various embodiments, an occurrence of synchronization may not count as synchronization for the purpose of identifying an episode of synchronization, tracking a condition, and/or controlling a therapy until the episode persists for a predetermined period of time (e.g., 1 minute), because longer periods of synchronization may evidence more meaningful coordination between the brain areas in some cases.

Characterizing synchronization between two or more brain areas may include determining the duration of an episode of synchronization. The duration of an episode may be measured from when the same measure of synchronization (e.g., increase in power levels of matching frequency bands of respective bioelectrical oscillations) rises above a threshold (e.g., frequencies of two different areas are within a predetermined amount of one another, such as 2 Hz, or the amplitude of the respective signals rise above a threshold) to the time that it falls below the threshold. As such, duration of synchronization may be used as a monitoring/titrating parameter in the manner that other parameters are used in FIGS. 1-3 and elsewhere herein.

In various embodiments, the time between exposure of the external sensory stimulus to the patient and the onset of synchronous activity between two or more brain areas (e.g., the time for a synchronization threshold to be crossed) is determined. This duration may be used as a metric for assessing the connectivity between brain areas and/or titrating therapy. For example, in some cases, faster synchronization of episodes over time is associated with better connectivity and improvement in a brain condition. A relatively slow rate of synchronization may trigger a change in a therapy parameter (e.g., an increase in an energy level parameter) while a faster rate of synchronization may validate therapy parameters and/or trigger a tapering of a therapy parameter if the improvement is more than enough and reflective of an improved patient condition. As such, duration to synchronization may be used as a monitoring/titrating parameter in the manner that other parameters are used in FIGS. 1-3 and elsewhere herein. The parameter may be, for example, improvement over time in the duration needed for brain areas to synchronize. In various cases, the duration for two brain areas to synchronize in some manner in response to a stimulus is 150-500 milliseconds in relatively healthy brain conditions. In some relatively problematic brain conditions, the duration may be 1-2 seconds.

As discussed herein, one or more criteria may be used to monitor and characterize synchronization between two brain areas and further titrate therapy. For example, in some embodiments, if a first parameter of a first brain area being monitored rises above an activation threshold indicating activation of a network function of that area, while a second parameter of a second brain area being monitored likewise rises above an activation threshold indicating activation of a network function of that area, then the simultaneous co-activation of the networks may be identified as synchronous activity. However, various embodiments may require more than simultaneous activation, and may further or alternatively require increases in power levels of a frequency band (e.g., the gamma frequency band) for each of two signals representing electrical activity of the different brain areas to make an identification of some degree of synchronization. For example, electrical activity of the two or more brain networks of a patient may need to oscillate at the same frequency, or close frequencies (e.g., within a predetermined frequency range of each other, such as 5 Hz), in order for an episode of synchronization to be identified. In some cases, synchronization will only be recognized when changes in frequency content (e.g., shifting frequency or increases in the power of a frequency band in the frequency domain) are observed for signals respectively associated with different brain areas. In some cases, synchronization will only be recognized when changes in signal amplitude accompanies the change in frequency content of the signals. One or both of electrical amplitude and oscillation phase may also be used to identify an episode of synchronization, or as an alternative to comparison of frequency characteristics between signals. Various embodiments may determine the frequency overlap of the networks, which can be a measure of the degree of synchronization. This may include determining the degree of frequency matching between the electrical oscillations between the two or more brain area. In various embodiments, matched frequency content of two signals will only be considered as indicative of synchronization when some other change in the signal is observed, such as increase in amplitude in the signals or the power level of the matched frequency increases in each signal. In various embodiments, matched frequency content of two signals will only be considered as indicative of synchronization if the matched frequency is the dominant frequency in the frequency domain in each signal (to distinguish from background activity), however in some embodiments the matched frequency may only need to be the dominant frequency in one signal. Various other criteria referenced herein can be used in any combination in various embodiments, such that an episode of synchronization between different brain areas is identified based on correspondence between one, two, three, or more different criteria.

Various embodiments concern characterizing the synchronization between two or more brain areas. Such characterization may include determining the degree of correspondence between activities of the two or more brain areas. Metrics of correspondence may include the degree of amplitude, phase, and/or frequency matching between electrical activities of the areas. Such characterizing may further include determining the duration of synchronization and/or the total time over a period of time that the patient's brain is in a state of synchronization (e.g., minutes per day). An output of a device can be made based on characterizing the synchronization, such as an indication on a display. Such characterization can be used to track the progression of a disease (with less synchronization indicating a worsening condition), titrate therapy, and/or assess improvements from therapy.

In various embodiments, synchronization of two or more brain areas is characterized not merely by frequency matching of bioelectrical activity in both areas, but is limited to frequencies in one or more bands. Different frequency bands are associated with different activities in the brain. Signals, including EEG and LFP signals, may exhibit multiple frequency components when converted to the frequency domain. The degree of synchronization for two or more brain areas may only be assessed based on the degree to which respective bioelectrical signals match within one or more frequency bands, such as within a frequency band that is associated with processing the kind of information of the external sensory stimulus exposed to the patient. For example, if a video of someone speaking is exposed to the patient, then one or more frequencies associated with processing sight and sound, or more particularly speech and facial processing functions, can be particularly analyzed to determine the degree of synchronization between the brain areas. Such a technique recognizes that some measurable synchronization may be seen in brain areas despite the brain having difficulty in synchronization of certain areas of the brain for certain functions.

In various embodiments, synchronization is only recognized for brain areas experiencing at least some threshold level of activity. For example, two brain areas may have a close match in oscillatory frequency, but the low signal amplitude level in one of the areas suggests that the brain area is in an idling mode. As such, two or more brain areas may only be considered to be synchronized, or in some improved degree of synchronization, when a metric of brain activity (e.g., bioelectrical signal amplitude) rises above a certain level for each brain area, and another metric (e.g., bioelectrical signal frequency) is used to determine whether, or the degree to which, the activity between two or more areas is synchronized. In this way, a parameter indicative of the level of activity of a brain area can be used to qualify the brain area for consideration for synchronization characterization with another brain area based on the same or another parameter.

Various embodiments of the present disclosure can include use of fMRI and other functional brain imaging techniques. Brain imaging can be used to determine which brain areas should be synchronizing and to guide therapy, fMRI can map brain activity to a 2D or 3D plot (e.g., on a display) allowing activated brain areas to be identified, usually indicated by being colored or otherwise highlighted. While fMRI is used as an exemplar in this disclosure, all other types of neural imaging are contemplated to be used in the same way, including MEG and PET scanning.

fMRI or other imaging technique can be used to monitor synchronization, identify which areas of the brain should synchronize, and/or for selecting target brain areas for monitoring and/or therapy delivery. For example, a patient can be placed in an fMRI field and then exposed to an external sensory stimulus. An fMRI display can light up to indicate which area(s) of the brain showed increased activity in response to the exposure. In some cases, this can be used as evidence of synchronization or lack thereof. In some other cases, this information can be used to identify brain areas that can then be targeted for synchronization monitoring to determine whether, and/or the degree to which, these areas are coordinating. In various cases, if synchronization is not indicated by further monitoring, then therapy may be appropriate and therefore initiated. As such, brain imaging can be used in conjunction with the techniques disclosed herein to guide monitoring and therapy delivery.

In various embodiments, the therapy is a continuous signal delivered using one, two, or more electrodes. In such embodiments, the electrodes used for sensing bioelectrical brain activity may be located some distance from the electrodes used for therapy delivery. In some embodiments, blanking in sensing and/or interruptions in delivery of an electrical therapy can be used to allow sensing of bioelectrical signals without concurrent electrical stimulation.

In various embodiments, electrical therapy is delivered directly to brain areas targeted for improvement in synchronization by locating an electrode within one or both targeted area and using the electrode as an cathode or anode during delivery of electrical energy, such as in the form of one or more pulses. In some cases it may be preferable to directly stimulate an associated brain area (e.g., remote from the targeted area) in an effort to bring about a change in a targeted area (e.g., the areas characterized by insufficient synchronization). In such cases, the targeted area may be electrically "down stream" from the associated brain area to which the electrical therapy is directly delivered, such that it is more effective and/or safer to electrically treat the targeted area remotely than directly. Stimulation delivered to the associated portion of the brain, rather than directly to the targeted portion, may have broader outputs to larger areas of the brain outside and including the targeted portion of the brain. In some cases, the targeted portion of the brain may be a posterior region relative to the associated portion of the brain, such that electrical stimulation of the associated portion reaches a larger area within the brain of the patient than electrical stimulation of one or more of the targeted portions directly. In various embodiments, the subthalamic nucleus may be stimulated in Parkinson's disease patient at approximately 130 Hz, although other areas and therapy parameters are contemplated. In the case of Alzheimer's disease patients, various therapies may be an electrical signal delivered to the thalamus or hippocampus of a patient at around 1-200 Hz. and at 0.5-10 volts with a pulse width of 50-200 microseconds, amongst other targets and parameters. These and other parameters may be used to address various other conditions.

The various techniques discussed herein may be performed, in whole or in part, by control circuitry using a processor. For example, a processor may compare frequency band characteristics of a first signal associated with a first brain area to frequency band characteristics of a second signal associated with a second brain area to determine whether the two signals (during the same period) exhibit substantially common frequencies, periods, power levels, and/or some other characteristic. If the processor determines that the power levels in a particular frequency band of the first and second signals are substantially similar (e.g., are within a threshold amount of each other or other both elevated relative to baseline levels), the processor may determine that the two areas of the brain are synchronized. If the processor does not make this determination; then an electrical therapy adjustment may automatically be made as discussed herein by the processor.

Figure 4:
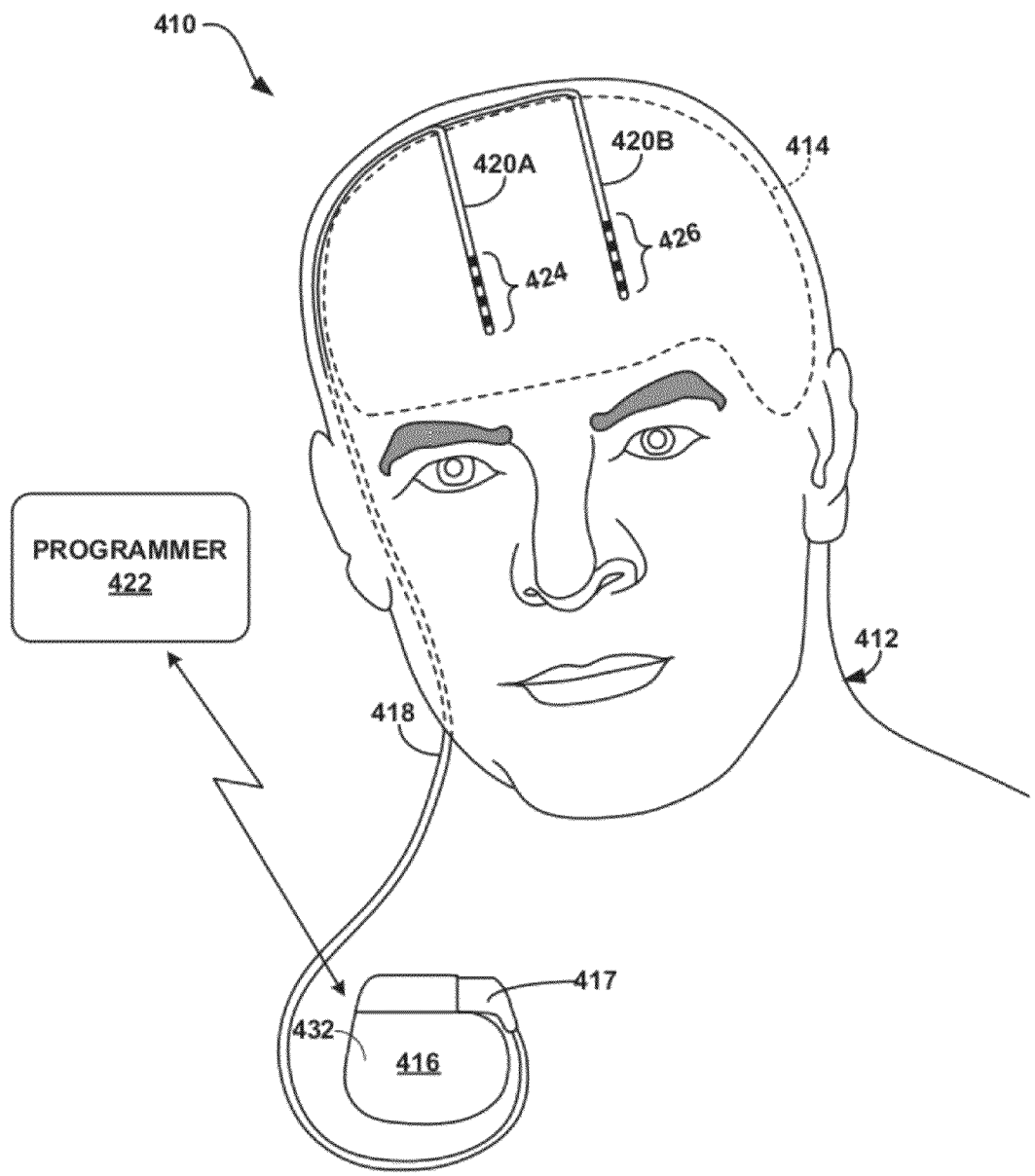
FIG. 4 is a conceptual diagram illustrating an example therapy system that delivers therapy to a patient to manage a disorder of the patient.

FIG. 4 is a conceptual diagram illustrating an example therapy system 410 that monitors a brain condition and/or delivers therapy to patient 412 to manage the brain condition of patient 412. System 410 includes implantable medical device (IMD) 416, lead extension 418, one or more leads 420A and 420B (collectively "leads 420") with respective sets of electrodes 424, 426, and medical device programmer 422. In various embodiments, IMD 416 includes a module with circuitry that senses electrical brain signals and identifies brain activity and conditions via the electrodes 424, 426 of leads 420A and 420B, respectively.

System 410 may monitor one or more bioelectrical brain signals of patient 412. For example, IMD 416 may include a sensing module (e.g., sensing module 444 of FIG. 5) that senses bioelectrical brain signals within one or more regions of brain 414. In the embodiment shown in FIG. 4, the signals may be sensed by electrodes 424, 426 and conducted to the sensing module within IMD 416 via conductors within the respective lead 420A, 420B. As described in further detail below, in some examples, control circuitry of IMD 416 or another device (e.g., programmer 422) monitors the bioelectrical signals within brain 414 of patient 412 with a processor to characterize synchronization, and/or perform the other functions referenced herein including those of FIGS. 1-3. Control circuitry of IMD 416 or another device (e.g., programmer 422) may control delivery of electrical therapy to brain 414 with a processor based on the characterization of synchronization in a manner that treats a brain condition of patient 412.

In some examples, the sensing module of IMD 416 may receive the bioelectrical signals from electrodes 424, 426 or other electrodes positioned to monitor bioelectrical brain signals of patient 412 (e.g., if housing 432 of IMD 416 is implanted in brain 414, an electrode of housing 432 can be used to sense bioelectrical brain signals and/or deliver stimulation to brain 414). Electrodes 424, 426 may also be used to deliver electrical stimulation from the therapy module to target sites within brain 414 as well as to sense brain signals within brain 414. However, IMD 416 can also use separate sensing electrodes to sense the bioelectrical brain signals. In some examples, the sensing module of MD 416 may sense bioelectrical brain signals via one or more of the electrodes 424, 426 that are also used to deliver electrical stimulation to brain 414. In other examples, one or more of electrodes 424, 426 may be used to sense bioelectrical brain signals while one or more different electrodes 424, 426 may be used to deliver electrical stimulation.

The bioelectrical brain signals monitored by IMD 416 may reflect changes in electrical current produced by the sum of electrical potential differences across brain tissue. Examples of the monitored bioelectrical brain signals include, but are not limited to, an EEG signal, an electrocorticogram (ECoG) signal, a LFP signal sensed from within one or more regions of brain 414, and/or action potentials from single cells within the brain 414 of one or more brain areas. These and other signals can be used to perform the various functions referenced herein, including detection of network activation and synchronization characterization.

As discussed herein, the monitored brain signals of patient 412 may be used to characterize synchronization of brain 414. Metrics that can be used to detect network activation and further characterize episodes of synchronization include time domain characteristics (e.g., an amplitude or phase) or frequency domain characteristics (e.g., a power level in one or more frequency bands) of the brain signals sensed by IMD 416 within one or more regions of brain 414. For example, the characteristic of the brain signals may include an absolute amplitude value or a root mean square amplitude value. In addition, the amplitude value may comprise an average, peak, mean, or instantaneous amplitude value over a period of time or a maximum amplitude or an amplitude in a particular percentile of the maximum (e.g., an amplitude value that represents 95% of the maximum amplitude value). Such peaks in amplitude or other parameter can be useful for identifying synchronization based on temporal correlation of changes in activity, such as burst of activity in two or more brain areas characterized by peaks in signal amplitude or increases in signal content (e.g., as measured by power) in certain frequency bands.

In various embodiments, the characteristic of the brain signal may include the frequency, amplitude, and phase of the bioelectrical brain signal(s) sensed within one or more regions of brain 414 of patient 412 associated with the different brain areas. The frequency, amplitude, and phase of the bioelectrical brain signal may indicate the oscillations in the brain signal and be used to determine the degree to which two brain areas are synchronized. The oscillations in the sensed bioelectrical brain signals may represent the rhythmic or repetitive neural activity in brain 414 when a particular network of an area is activated to perform a particular function. The neural oscillations may be determined based on one or more frequency domain characteristics of the bioelectrical brain signal. The neural oscillations or other characteristics of the signals of the different areas can be compared to one another to assess synchronicity of the different areas and titrate therapy.

Different frequency bands are associated with different activity in the brain. One example of the frequency bands that can be used is shown in Table 1:

TABLE 1

| Frequency (f) Band Hertz (Hz) | Frequency Information |
| --- | --- |
| f < 4 Hz | δ (delta frequency band) |
| 4 Hz ≤ f ≤ 8 Hz | theta frequency band |
| 8 Hz ≤ f ≤ 13 Hz | α (alpha frequency band) |
| 13 Hz ≤ f ≤ 35 Hz | β (beta frequency band) |
| 35 Hz ≤ f ≤ 100 Hz | γ (gamma frequency band) |
| 100 Hz ≤ f ≤ 200 Hz | high γ (high gamma frequency band) |

In various embodiments, IMD 416 may deliver therapy to any suitable portion of brain 414 that may play a rote in affecting synchronization of brain areas. In some embodiments, system 410 may deliver therapy to patient 412 to manage a neurological disorder of patient 412. For example, system 410 may provide therapy to correct a brain disorder and/or manage symptoms of a neurodegenerative brain condition. In some embodiments, system 410 may provide therapy to patient 412 to manage Schizophrenia, Alzheimer's disease, autism, cognitive impairment, or other brain condition that can be characterized by insufficient coordination between brain areas. Patient 412 ordinarily will be a human patient. In some cases, however, system 410 and the techniques disclosed herein may be applied to other mammalian non-human or non-mammalian patients. While examples of the disclosure are described with regard to tracking and treatment of a cognitive disorder such as Schizophrenia, in other examples, system 410 may track and/or provide therapy to manage symptoms of other patient conditions.

IMD 416 may include a module that includes a stimulation generator that generates and delivers electrical stimulation therapy to one or more regions of brain 414 of patient 412 via the electrodes 424, 426 of leads 420A and 420B, respectively. In the example shown in FIG. 4, system 410 may be referred to as deep brain stimulation system because IMD 416 may provide electrical stimulation therapy directly to tissue within brain 414, e.g., a tissue site under the dura mater of brain 414. In other embodiments, leads 420 may be positioned to sense brain activity and/or deliver therapy to a surface of brain 414, such as the cortical surface of brain 414.

In the example shown in FIG. 4, IMD 416 may be implanted within a subcutaneous pocket below the clavicle of patient 412. In other embodiments, IMD 416 may be implanted within other regions of patient 412, such as a subcutaneous pocket in the abdomen or buttocks of patient 412, proximate the cranium, or on/in the cranium of patient 412, implanted lead extension 418 is coupled to IMD 416 via a connector block (also referred to as a header), which may include, for example, electrical contacts that electrically couple to respective electrical contacts on lead extension 418. The electrical contacts electrically couple the electrodes 424, 426 carried by leads 420 to IMD 416. Lead extension 418 traverses from the implant site of IMD 416 within a chest cavity of patient 412, along the neck of patient 412 and through the cranium of patient 412 to access brain 414. Generally, IMD 416 is constructed of a biocompatible material that resists corrosion and degradation from bodily fluids. MD 416 may comprise a hermetic housing 432 to substantially enclose control circuitry, such as a processor and memory. In various embodiments, IMD 416 may be implanted only in the head of the patient (e.g., under the scalp) and not in the chest and neck regions.

Electrical stimulation may be delivered to one or more regions of brain 414, which may be selected based on many factors, such as the type of patient condition for which system 410 is implemented to manage and which brain areas evidence a lack of synchronization. In some examples, leads 420 may be implanted within the right and left hemispheres of brain 414 (e.g., as illustrated in FIG. 4) while, in other examples, both of leads 420 may be implanted within one of the right or left hemispheres. Other implant sites for leads 420 and IMD 416 are contemplated. For example, in some examples, IMD 416 may be implanted on or within the cranium. In addition, in some examples, leads 420 may be coupled to a single lead that is implanted within one hemisphere of brain 414 or implanted through both right and left hemispheres of brain 414.

Leads 420 may be positioned to deliver electrical stimulation to one or more target tissue sites within brain 414 to manage patient symptoms associated with a disorder of patient 412. Targeted tissues may be the tissues identified 210 and 215 as being associated with the brain areas of interest lacking synchronization. Leads 420 may be implanted to position electrodes 424, 426 at desired locations of brain 414 through respective holes in the cranium. Leads 420 may be placed at any location within brain 414 such that electrodes 424, 426 are capable of providing electrical stimulation to target tissue sites within brain 414 during treatment. In some embodiments, leads may be placed such that electrodes 424, 426 directly contact or are otherwise proximate targeted tissue of a particular brain area.

In the example shown in FIG. 4, electrodes 424, 426 of leads 420 are shown as ring electrodes. Ring electrodes may be relatively easy to program and are typically capable of sensing and/or delivering an electrical field to any tissue adjacent to leads 420 (e.g., in all directions away from an outer perimeter of leads 420). In other examples, electrodes 424, 426 of leads 420 may have different configurations. For example, electrodes 424, 426 of leads 420 may have a complex electrode array geometry that is capable of producing shaped electrical fields. The complex electrode array geometry may include multiple electrodes (e.g., partial ring or segmented electrodes) around the perimeter of each lead 420, rather than a ring electrode. In this manner, electrical brain sensing and/or electrical stimulation may be associated with a specific direction from leads 420 (e.g., in a direction less than around the entire outer perimeter of leads 420) to enhance directional sensing and/or therapy efficacy and reduce possible adverse side effects from stimulating a large volume of tissue in the case of stimulation. As such, electrodes can be positioned to stimulate targeted tissue and avoid stimulating non-targeted tissue.

In some embodiments, outer housing 432 of IMD 416 may include one or more stimulation and/or sensing electrodes. For example, housing 432 can comprise an electrically conductive material that is exposed to tissue of patient 412 when IMD 416 is implanted in patient 412, or an electrode can be attached to housing 432. In stimulation, the housing 432 electrode can serve as an anode and an electrode in the brain can serve as the cathode, for example. In some examples, leads 420 may have shapes other than elongated cylinders as shown in FIG. 4. For example, leads 420 may be paddle leads, spherical leads, bendable leads, or any other type of shape effective in treating patient 412.

In the examples described herein, for treatment of a cognitive disorder (e.g., schizophrenia), leads 420 may be implanted to deliver electrical stimulation to various portions of brain 414 of patient 412, such as the thalamus, including anterior thalamic nucleus and the interior thalamus, cerebellum, basil ganglia, brain stem, the internal capsule, cortex, including the prefrontal cortex, the frontal cortex, the orbitofrontal cortex, and the cingulate cortex (including the anterior cingulate gyrus), the fornix, the mammillary bodies, the mammillothalamic tract (mammillothalamic fasciculus), the hippocampus, the Basal Nucleus of Meynert (NBM), the medial septal nucleus, the locus coeruleus, the raphe nucleus, the substantia nigra, the amygdala, the hypothalamus, and other portions of the thalamus and the limbic system.

Stimulation generator 442, under the control of processor 440, generates stimulation signals for delivery to patient 412 via selected combinations of electrodes 424, 426. Processor 440 of control circuitry controls stimulation generator 442 according to stimulation programs 452 stored in memory 441 to apply particular stimulation parameter values specified by one or more programs, such as amplitude, pulse width, and pulse rate, in accordance with the various embodiments of this disclosure. In some examples, stimulation generator 442 generates and delivers stimulation signals to one or more target portions of brain 414 via a select combination of electrodes 424, 426

Leads 420 may be implanted within a desired location of brain 414 via any suitable technique, such as through respective burr holes in a skull of patient 412 or through a common burr hole in the cranium. Leads 420 may be placed at any location within brain 414 such that electrodes 424, 426 of leads 420 are capable of sensing electrical activity of the brain areas of (e.g., those thought to have inadequate connectivity resulting in loss of synchronization) and/or providing electrical stimulation to targeted tissue for treatment (e.g., to stimulate to facilitate synchronization of brain areas).

In some examples, a processor of system 410 (e.g., a processor of control circuitry of programmer 422 and/or IMD 416) controls delivery of electrical stimulation by activating electrical stimulation, deactivating electrical stimulation, increasing the intensity of electrical stimulation, or decreasing the intensity of electrical stimulation delivered to brain 414 to titrate electrical stimulation therapy to facilitate synchronization of two or more brain areas. Therapy can be started, stopped, and/or changed by processor 440 in any manner and based on any parameter or finding as discussed herein, including that the therapy drives brain network activation.

System 410 may also store a plurality of stimulation programs (e.g., a set of electrical stimulation parameter values), and at least one stimulation program may be associated with at least one type or degree of synchronization and/or different brain areas. A processor of control circuitry of IMD 416 or programmer 422 may select a stored stimulation program that defines electrical stimulation parameter values for delivery of electrical stimulation to brain 414 based on a characterization of synchronization or what brain areas are showing a lack of synchronization (e.g., different predetermined or learned therapy parameters for different combinations of two or more brain areas, each program tailored for each different combination of brain areas). Where IMD 416 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities.

External programmer 422 wirelessly communicates with IMD 416 as needed to provide or retrieve information. For example, external programmer 422 may receive sensed data and/or information regarding one or more episodes of synchronization from IMD 416, as well as send therapy program information to IMD 416. Programmer 422 is an external computing device that the user, e.g., the clinician and/or patient 412, may use to communicate with IMD 416. For example, programmer 422 may be a clinician programmer that the clinician uses to communicate with IMD 416 and program one or more therapy programs for IMD 416. Additionally or alternatively, programmer 422 may be a patient programmer that allows patient 412 to input information (e.g., a self evaluated assessment), select programs, and/or view and modify therapy parameters.

Programmer 422 may be a hand-held computing device with a display viewable by the user and an interface for providing input to programmer 422 (i.e., a user input mechanism). For example, programmer 422 may include a small display screen (e.g., a liquid crystal display (LCD) or a light emitting diode (LED) display) that presents information to the user, such as external sensory stimuli in the form of graphics. Programmer 422 may include a speaker for providing auditory sensory stimuli to the patient. In addition, programmer 422 may include a touch screen display, keypad, buttons, a peripheral pointing device or another input mechanism that allows the user to navigate though the user interface of programmer 422 and provide input. The screen (not shown) of programmer 422 may be a touch screen that allows the user to provide input directly to the user interface shown on the display. The user may use a stylus or their finger to provide input to the display.

In other examples, programmer 422 may be a larger workstation or a separate application within another multi-function device, rather than a dedicated computing device. For example, the multi-function device may be a notebook computer, tablet computer, workstation, cellular phone, personal digital assistant or another computing device. Such devices may be able to present sensory stimuli to a patient.

When programmer 422 is configured for use by the clinician, programmer 422 may be used to transmit initial programming information to IMD 416. This initial information may include hardware information, such as the type of leads 420, the arrangement of electrodes 424, 426 on leads 420, the position of leads 420 within brain 414, initial programs defining therapy parameter values, and any other information that may be useful for programming into IMD 416. Programmer 422 may also be capable of completing functional tests (e.g., measuring the impedance of electrodes 424, 426 of leads 420).

The clinician may also store therapy programs within IMD 416 with the aid of programmer 422. During a programming session, the clinician may determine one or more stimulation programs that may effectively bring about a therapeutic outcome that treats a brain condition, such as facilitating synchronization of two or more brain areas. For example, the clinician may select one or more electrode combinations with which stimulation is delivered to brain 414 to facilitate synchronization. During the programming session, the clinician may evaluate the efficacy of the one or more electrode combinations based on one or more findings of an fMRI, patient self reporting, LFP, EEG, or some other parameters for characterizing synchronization of brain areas of the patient 412. In some examples, programmer 422 may assist the clinician in the creation/identification of stimulation programs by providing a methodical system for identifying potentially effective stimulation parameter values, such as by instructing that certain external sensory stimuli be exposed to the patient or displaying stimuli on the programmer 422 interface. In some examples, the control circuitry of programmer 422 may calculate and display one or more therapy metrics for evaluating and comparing therapy programs available to delivery of therapy from IMD 416 to patient.

Programmer 422 may also provide an indication to patient 412 when therapy is being delivered which may aid the assessment of therapy efficacy. For example, upon seeing that therapy is being delivered the patient may evaluate whether he or she seems to have a clearer state of mind and/or has cessation of symptoms (e.g., lack of errant voices in his or her head or a clearer state of mind) by answering questions presented on the programmer 422.

Whether programmer 422 is configured for clinician or patient use, programmer 422 is configured to communicate with IMD 416 and, optionally, another computing device, via wireless communication. Programmer 422, for example, may communicate via wireless communication with IMD 416 using radio frequency (RF) telemetry techniques known in the art. Programmer 422 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 422 may also communicate with other programming or computing devices via exchange of removable media, such as magnetic or optical disks, memory cards or memory sticks. Further, programmer 422 may communicate with IMD 416 and another programmer via remote telemetry techniques known in the art, communicating via a local area network (LAN), wide area network (WAN), public switched telephone network (PSTN), or cellular telephone network, for example.

FIG. 4 is a functional block diagram illustrating components of IMD 416. In the example shown in FIG. 4, IMD 416 includes processor 440, memory 441, stimulation generator 442, and sensing module 444, which can be control circuitry as means for performing functions as described herein (e.g., delivering a therapy, sensing signals, assessing synchronization, and titrating the therapy). Memory 441 may include any volatile or non-volatile media, such as a random access memory (RAM), read only memory (ROM), non-volatile RAM (NVRAM), electrically erasable programmable ROM (EEPROM), flash memory, and the like. Memory 441 may store computer-readable instructions that, when executed by processor 440, cause IMD 416 to perform various functions described herein.

The steps, procedures, techniques, etc. referenced herein may be carried out in part by, for example, software instructions, such as those used to define a software or computer program. The computer-readable medium may store instructions. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the actions described herein.

Two or more brain areas may be monitored by one signal, and synchronization may be detected by two or more patterns respectively associated with the two or more brain areas or by a biomarker indicative of synchronous activity of the two or more areas. Processor 440 may determine whether a sensed bioelectrical brain signal includes a biomarker (e.g., a particular power level of a particular frequency band) indicative of synchronization. Processor 440 may analyze a sensed bioelectrical signal amplitude, frequency, correlation with a template, or a specific stored value. For example, the instantaneous, peak, lowest or average amplitude of the bioelectrical brain signal over a period of time (which can be predetermined) may be compared to an amplitude threshold, for characterizing synchronous activation of two or more brain networks.

As another technique that can be implemented by a processor 440 as part of control circuitry for synchronization detection, memory 441 may store portions of bioelectrical brain signals (e.g., waveforms or specific values of signal characteristics) previously sensed within brain 414 of patient that corresponds to synchronization of brain areas that is confirmed by fMRI. In some examples, the stored bioelectrical brain signals can be used as a template to determine whether a particular sensed bioelectrical brain signal is indicative of synchronization of two or more particular brain areas. As an example of a signal processing technique that processor 440 may employ to determine whether the bioelectrical brain signal includes the biomarker associated with synchronization, processor 440 may analyze the bioelectrical brain signal with feature correlation, temporal correlation, or frequency correlation with a template signal, or combinations thereof. As another example, a slope of the amplitude of the bioelectrical brain signal over time or timing between inflection points or other critical points in the pattern of the amplitude of the bioelectrical brain signal over time may be compared to trend information stored in memory. A correlation between the inflection points in the amplitude waveform of the bioelectrical brain signal or other critical points and a template may indicate the bioelectrical brain signal includes the biomarker indicative of the synchronization of two or more brain areas, which may be validated by comparison to fMRI images and/or controlled external sensory stimulus tests described herein, to characterize synchronization and/or titrate therapy delivery. However, various embodiments may function in alternative manners.

As another technique for network activation detection, processor 440 as part of control circuitry may perform temporal correlation by sampling the waveform generated by a sensed bioelectrical brain signal with a sliding window and comparing the waveform with a template waveform stored in memory that is associated with activation of a particular brain area or two or more areas. For example, processor 440 may perform a correlation analysis by moving a window along a digitized plot of the amplitude waveform of a sensed bioelectrical brain signal at regular intervals, such as between about one millisecond to about ten millisecond intervals, to define a sample of the bioelectrical brain signal. The sample window is slid along the plot until a correlation is detected between the waveform of the template and the waveform of the sample of the brain signal defined by the window. By moving the window at regular time intervals, multiple sample periods are defined. The correlation may be detected by, for example, matching multiple points between the template waveform and the waveform of the plot of the sensed bioelectrical brain signal over time, or by applying any suitable mathematical correlation algorithm between the sample in the sampling window and a corresponding set of samples stored in the template waveform. The template may be validated by comparison to fMRI images and/or controlled external sensory stimulus tests described herein.

As shown, the set of electrodes 424 of lead 420A includes electrodes 424A, 424B, 424C, and 424D, and the set of electrodes 426 of lead 42013 includes electrodes 426A, 426B, 426C, and 426D. Processor 440 may control switch module 446 to apply the stimulation signals generated by stimulation generator 442 to selected combinations of electrodes 424, 426. In particular, switch module 446 may couple stimulation signals to selected conductors within leads 420, which, in turn, deliver the stimulation signals across selected electrodes 424, 426. Switch module 446 may be a switch array, switch matrix, multiplexer, or any other type of switching module configured to selectively couple stimulation energy to selected electrodes 424, 426 and to selectively sense bioelectrical brain signals with selected electrodes 424, 426. Hence, stimulation generator 442 is coupled to electrodes 424, 426 via switch module 446 and conductors within leads 420. In some examples, however, IMD 416 does not include switch module 446.

Sensing module 444 is configured to sense bioelectrical brain signals of patient 412 via a selected subset of electrodes 424, 426, or with one or more electrodes 424, 426 and at least a portion of a conductive outer housing 432 of IMD 416, an electrode on an outer housing of IMD 416, or another reference. Processor 440 may control switch module 446 to electrically connect sensing module 444 to selected electrodes 424, 426. In this way, sensing module 444 may selectively sense bioelectrical brain signals with different combinations of electrodes 424, 426 (and/or a reference other than an electrode 424, 426).

Clinician, processor 440 of IMD 416, or a processor of another device, such as programmer 422, may determine the one or more biomarkers indicative of network synchronization based on the bioelectrical brain signal(s). The biomarkers may be selected by the clinician or automatically by a processor of control circuitry, and may be selected as the signal characteristics that distinguish the bioelectrical brain signal sensed during synchronization of two or more brain areas from a bioelectrical brain signal sensed at other times without such synchronization. The biomarker may be validated by comparison to fMRI images and/or controlled external sensory stimulus tests described herein. The biomarker can then serve as a synchronization threshold or other indicator for subsequent detection of synchronization.

Processor 440 as part of control circuitry may monitor bioelectrical brain signals sensed by sensing module 444 in any suitable manner in order to compare and characterize the degree of synchronization between the signals and/or brain areas. For example, sensing module 444 may directly sense one or more bioelectrical brain signals, e.g., a LFP, via one or more of electrodes 424, 426 at a particular point within a portion of brain 414 that concerns a first and/or second area of the brain, and processor 440 may monitor the bioelectrical brain signal. In some examples, processor 440 may compare one or more characteristics (e.g., amplitude or frequency) of the bioelectrical brain signal(s) to each other and/or to a threshold associated with synchronization to characterize the degree of synchronization present. Memory 441 may store information related to threshold values for signal characteristics that demarcate synchronization, and processor 440 may compare characteristics of the sensed bioelectrical brain signals to the stored threshold values to characterize synchronization.

In various embodiments, system 410 may include one or more external electrodes positioned on the outer surface of the cranium of patient 412 that can sense and generate a bioelectrical brain signal, e.g., an EEG signal, that can be used to characterize synchronization of brain areas. Such characterization of brain area synchronization may use the techniques discussed herein for characterizing synchronization via internally sensed signals (e.g., comparing signals, frequency or other parameter correspondence, a biomarker, template, and/or other technique).

Although sensing module 444 is incorporated into a common housing 432 with stimulation generator 442 and processor 440, in other examples, sensing module 444 is in a physically separate outer housing from outer housing 432 of IMD 416 and communicates with processor 440 via wired or wireless communication techniques.

Sensing of brain signals and detecting events, such as synchronization, can be implemented in view of commonly assigned U.S. Provisional Patent Application No. 61/527,387, filed on Aug. 25, 2011, by Carlson et al., titled METHOD AND APPARATUS FOR DETECTING A BIOMARKER IN THE PRESENCE OF ELECTRICAL STIMULATION, which is incorporated by reference herein in its entirety. Furthermore, setting algorithms for event detection, such as training an algorithm for detecting synchronization, can be implemented in view of commonly assigned U.S. Pat. App. No. 2010/0280335 to Carlson et al., which is entitled "PATIENT STATE DETECTION BASED ON SUPERVISED MACHINE LEARNING BASED ALGORITHM" filed Nov. 4, 2010; and U.S. Pat. App. No. 2010/0280334 to Carlson et al., which is entitled "PATIENT STATE DETECTION BASED ON SUPPORT VECTOR MACHINE BASED ALGORITHM" filed Nov. 4, 2010, which are incorporated herein by reference in their entireties.

Telemetry module 448 supports wireless communication between IMD 416 and an external programmer 422 or another computing device under the control of processor 440. Processor 440 of IMD 416 may receive, as updates to sensing and/or stimulation programs, values for stimulation parameters such as amplitude and electrode combination information from programmer 422 via telemetry module 448. The updates to the stimulation, sensing, or other programs may be stored within stimulation programs 452 of memory 441. Telemetry module 448 in IMD 416, as well as telemetry modules in other devices and systems described herein, such as programmer 422, may accomplish communication by RF communication techniques. In addition, telemetry module 448 may communicate with external medical device programmer 422 via proximal inductive interaction of MD 416 with programmer 422. Accordingly, telemetry module 448 may send information to external programmer 422 on a continuous basis, at periodic intervals, or upon request from IMD 416 or programmer 422. For example, processor 440 may transmit sensed signals and/or synchronization information to programmer 422 via telemetry module 448.

Power source 450 delivers operating power to various components of IMD 416. Power source 450 may include a small rechargeable or non-rechargeable battery and a power generation circuit to produce the operating power. Recharging may be accomplished through proximal inductive interaction between an external charger and an inductive charging coil within IMD 416. In some examples, power requirements may be small enough to allow IMD 416 to utilize patient motion and implement a kinetic energy-scavenging device to trickle charge a rechargeable battery. In various embodiments, traditional batteries may be used.

Figure 5:
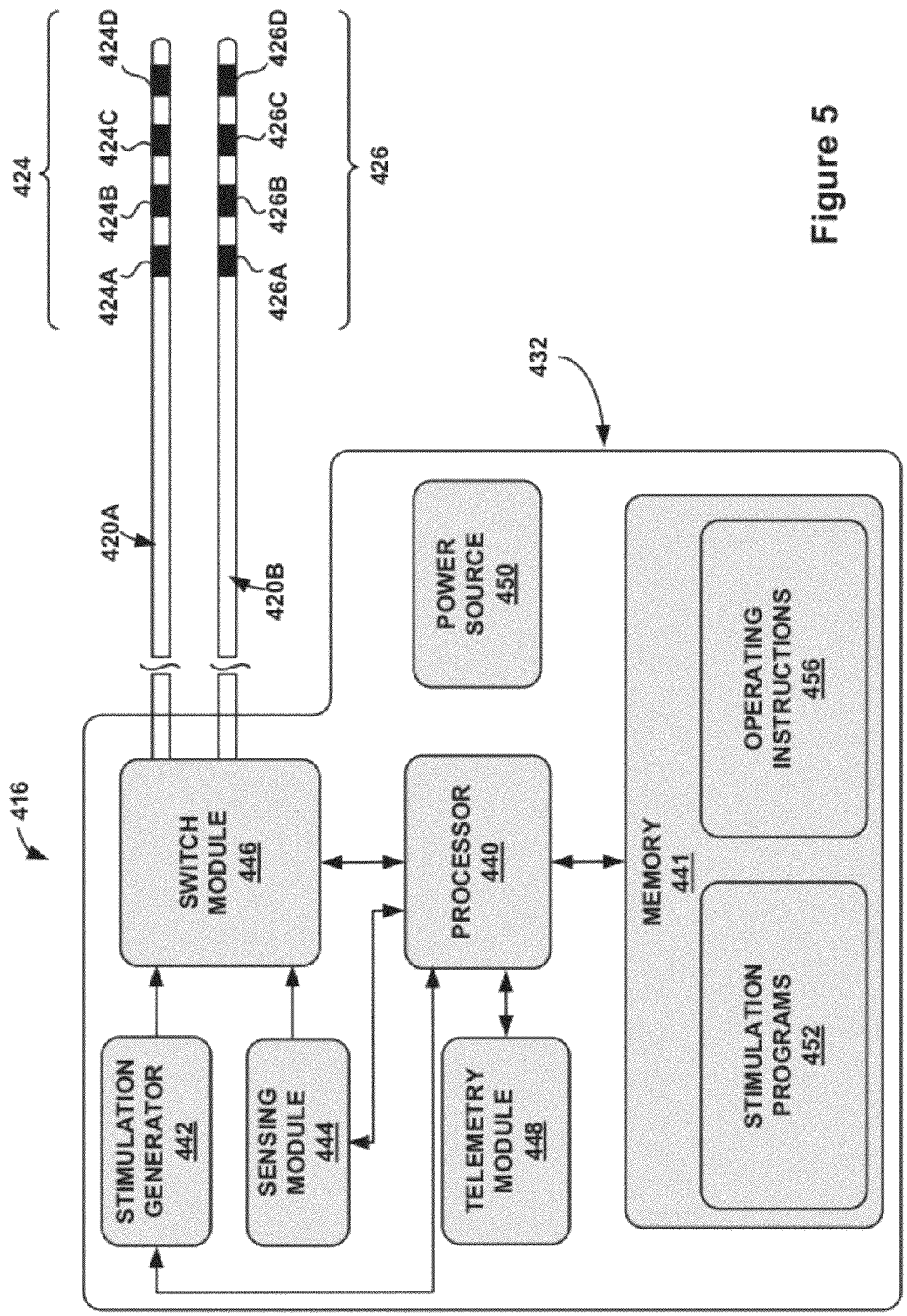
FIG. 5 is a functional block diagram illustrating control circuitry of a medical device.

Although the control circuitry of FIG. 5 is illustrated and described in terms of an implantable device, the control circuitry could alternatively be embodied in an at least particularly external device and, depending on the therapy and/or circuitry configuration, may be wholly external.

The techniques described in this disclosure, including those of FIGS. 1-5 and those attributed to programmer, IMD, processor, and/or control circuitry, or various constituent components, may be implemented wholly or at least in part, in hardware, software, firmware or any combination thereof. A processor, as used herein, refers to any number and/or combination of a microprocessor, a digital signal processor (DSP), an application specific integrated circuit (ASIC), a field-programmable gate array (FPGA), microcontroller, discrete logic circuitry, processing chip, gate arrays, and/or any other equivalent integrated or discrete logic circuitry. "Control circuitry" as used herein refers to at least one of the foregoing logic circuitry as a processor, alone or in combination with other circuitry, such as memory or other physical medium for storing instructions, as needed to carry about specified functions (e.g., processor and memory having stored program instructions executable by the processor for characterizing synchronization between two or more brain areas and titrating an electrical therapy). The functions referenced herein and those functions of FIGS. 1-5, may be embodied as firmware, hardware, software or any combination thereof as part of control circuitry specifically configured (e.g., with programming) to carry out those functions, such as in means for performing the functions referenced herein. The steps described herein may be performed by a single processing component or multiple processing components, the latter of which may be distributed amongst different coordinating devices (e.g., an IMD and an external programmer). In this way, control circuitry may be distributed between multiple devices, including an implantable medical device and an external medical device in various systems. In addition, any of the described units, modules, or components may be implemented together or separately as discrete but interoperable logic devices of control circuitry. Depiction of different features as modules or units is intended to highlight different functional aspects and does not necessarily imply that such modules or units must be realized by separate hardware or software components and/or by a single device. Rather, functionality associated with one or more module or units, as part of control circuitry, may be performed by separate hardware or software components, or integrated within common or separate hardware or software components of the control circuitry.

When implemented in software, the functionality ascribed to the systems, devices and control circuitry described in this disclosure may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of control circuitry. The instructions may be executed to support one or more aspects of the functionality described in this disclosure.

While schizophrenia is generally used as an exemplar for describing various aspects of the present disclosure, it is contemplated that the techniques and devices could be applied to other brain conditions, such as Parkinson's disease, mild cognitive impairment, and traumatic brain damage, among others. Furthermore, it is contemplated that various brain conditions may be characterized by the desynchronization between areas and loss of coordination between brain networks. As such, various embodiments concern facilitating synchronization of two or more areas of the brain of a patient by delivery and titration of a sub-threshold electrical therapy to address such desynchronization. While the present disclosure generally refers to monitoring two or more areas of a patient's brain and titrating a therapy to facilitate synchronization of the two or more areas, it is contemplated that two or more neural networks can be monitored and therapy can be titrated to facilitate synchronization of the two or more neural networks (not specific to two particular brain areas) in any equivalent way as brain areas are monitored/therapeutically treated as referenced herein. The various techniques, features, and components discussed herein in various embodiments are applicable to various other embodiments in different configurations and combinations, as the present disclosure makes use of examples to illustrate options which are not limited to the specific embodiments presented. As such, each example embodiment should be understood to be combinable and modifiable in view of the other embodiments presented herein.

We claim:

1. A method of treating a condition of a brain of a patient, the method comprising:
   delivering an electrical therapy to the brain of the patient;
   monitoring one or more bioelectrical brain signals indicative of synchronization between two or more areas of the brain; and
   titrating the electrical therapy to improve synchronization between the two or more areas of the brain based on the one or more bioelectrical brain signals, the synchronization between the two or more areas of the brain occurring in response to an external sensory stimulus, wherein the external sensory stimulus tests whether the electrical therapy improves synchronization between the two or more areas of the brain, wherein the electrical therapy does not independently cause activation of either of the two or more areas of the brain, and wherein delivering, monitoring, and titrating are performed at least in part by control circuitry.

2. The method of claim 1, further comprising controlling exposure of the patient to the external sensory stimulus.

3. The method of claim 2, wherein:
   the external sensory stimulus comprises at least two different types of associated stimulus; and
   the two or more areas of the brain are respectively associated with brain functions for processing the at least two different types of associated stimulus.

4. The method of claim 3, wherein:
   the external sensory stimulus comprises video and associated sounds of activity in the video; and
   the two or more areas of the brain are respectively associated with brain functions for processing sight and sound.

5. The method of claim 1, wherein the external sensory stimulus comprises only a single stimulus.

6. The method of claim 1, wherein the external sensory stimulus comprises a sensory-motor stimulus.

7. The method of claim 1, wherein monitoring the one or more signals comprises determining a measure of synchronization between the two or more areas of the brain based on two or more bioelectrical brain signals respectively generated by the two or more areas of the brain.

8. The method of claim 7, wherein the measure of synchronization measures consistency in the difference between one or both of the frequencies and phases of a first signal from one of the two or more areas of the brain and a second signal from another of the two or more areas of the brain.

9. The method of claim 1, wherein the electrical therapy comprises a low frequency electrical carrier signal that facilitates synchronization between the two or more areas of the brain.

10. The method of claim 1, wherein the electrical therapy is delivered at a beta or a gamma frequency range.

11. The method of claim 1, wherein the electrical therapy addresses a cognitive disorder, wherein increased synchronization between the two or more areas of the brain improves symptoms of the cognitive disorder.

12. The method of claim 1, wherein the electrical therapy is delivered by one or more electrodes implanted within the brain proximate to the thalamus.

13. The method of claim 1, further comprising determining the degree of synchronization between the two or more areas of the brain based on the one or more bioelectrical brain signals.

14. The method of claim 1, wherein titrating the electrical therapy comprises:
   changing, based on the one or more bioelectrical brain signals, one or more electrical therapy parameters of the electrical therapy; and
   delivering, according to the changed one or more electrical therapy parameters, the electrical therapy to the brain of the patient.

15. A system comprising:
   one or more sensors configured to receive one or more bioelectrical signals indicative of brain activity;
   a stimulation generator configured to deliver electrical therapy to the brain of a patient; and
   control circuitry configured to determine a measure of synchronization between two or more areas of the brain of the patient based on the one or more bioelectrical signals and titrate delivery of the electrical therapy based on the measure of synchronization to improve synchronization between the two or more areas of the brain, wherein the electrical therapy is titrated by the control circuitry such that synchronization between the two or more areas of the brain occurs in response to external sensory stimulus, wherein the external sensory stimulus tests whether the electrical therapy improves synchronization between the two or more areas of the brain, and wherein the electrical therapy does not independently cause activation of either of the two or more areas of the brain.

16. The system of claim 15, wherein the measure of synchronization measures consistency in the difference between the phases of a first signal from one of the two or more areas of the brain and a second signal from another of the two or more areas of the brain.

17. The system of claim 15, wherein the measure of synchronization measures frequency similarity between a first signal from one of the two or more areas of the brain and a second signal from another of the two or more areas of the brain.

18. The system of claim 15, wherein the electrical therapy comprises a low frequency electrical carrier signal that facilitates synchronization between the two or more areas of the brain.

19. The system of claim 15, wherein the stimulation generator is configured to deliver the electrical therapy within one or both of a beta frequency range and a gamma frequency range.

20. The system of claim 15, further comprising a user interface, wherein the control circuitry is configured to initiate exposure of the external sensory stimuli to the patient on a user interface.

21. The system of claim 15, wherein at least one of the two or more areas of the brain is associated with a brain function for processing the one or more external sensory stimuli to which the patient is exposed.

22. A system, comprising:
   means for delivering an electrical therapy to a brain of a patient;
   means for monitoring one or more bioelectrical brain signals indicative of synchronization between two or more areas of the brain; and
   means for titrating the electrical therapy to improve synchronization between the two or more areas of the brain based on the one or more bioelectrical brain signals, wherein the electrical therapy is titrated such that the synchronization between the two or more areas of the brain occurs in response to external sensory stimulus, wherein the external sensory stimulus tests whether the electrical therapy improves synchronization between the two or more areas of the brain, and wherein the electrical therapy does not independently cause activation of either of the two or more areas of the brain.

* * * * *